(12) United States Patent
Henkel et al.

(10) Patent No.: US 6,730,017 B2
(45) Date of Patent: May 4, 2004

(54) PRESSURE BASED SPONTANEOUS INFLATION INHIBITOR WITH PENILE PUMP IMPROVEMENTS

(75) Inventors: Gregory J. Henkel, Chanhassen, MN (US); Larry E. Waldack, Bloomington, MN (US); Charles C. Kuyava, Eden Prairie, MN (US); Randy L. Morningstar, Brooklyn Park, MN (US); John G. Almli, Chaska, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 10/010,498

(22) Filed: Dec. 3, 2001

(65) Prior Publication Data

US 2002/0082473 A1 Jun. 27, 2002

Related U.S. Application Data

(63) Continuation-in-part of application No. 09/749,292, filed on Dec. 27, 2000, now abandoned.
(60) Provisional application No. 60/295,326, filed on Jun. 1, 2001.

(51) Int. Cl.$^7$ .................................................. A61F 5/00
(52) U.S. Cl. ...................................... 600/40; 623/11.11
(58) Field of Search ..................... 600/38–41, 29–32; 128/171, 625, 843; 623/11.11

(56) References Cited

U.S. PATENT DOCUMENTS

| | | |
|---|---|---|
| 988,120 A | 3/1911 | Lott |
| 1,863,057 A | 6/1932 | Innes |
| 3,312,215 A | 4/1967 | Silber |
| 3,344,791 A | 10/1967 | Foderick |
| 3,397,699 A | 8/1968 | Kohl |
| 3,503,400 A | 3/1970 | Osthagen et al. |
| 3,642,004 A | 2/1972 | Osthagen et al. |
| 3,731,670 A | 5/1973 | Loe |
| 3,797,478 A | 3/1974 | Walsh et al. |
| 3,812,841 A | 5/1974 | Isaacson |
| 3,954,102 A | 5/1976 | Buuck |
| 4,222,377 A | 9/1980 | Burton |
| 4,267,829 A | 5/1981 | Burton et al. |
| 4,344,434 A | 8/1982 | Robertson |
| 4,383,525 A | 5/1983 | Scott et al. |

(List continued on next page.)

FOREIGN PATENT DOCUMENTS

DE 2537506 3/1977

*Primary Examiner*—John P. Lacyk
(74) *Attorney, Agent, or Firm*—Jeffrey J. Hohenshell

(57) ABSTRACT

A pump assembly for a penile implant is provided having a mechanism which prevents spontaneous inflation of the cylinders implanted within the patient. The pump assembly has an actuating bar with ribs to enhance the spring force applied to a flow valve, a support structure to support and appropriately position the actuating bar, and a check valve made of metal with a segment covered with a plastic material. The preventative mechanism uses overpressure generated by the reservoir during unintentional compression to effectively seal the cylinders from unintended fluid flow. The prevention mechanism itself creates all necessary forces to prevent the undesired fluid flow to the cylinders. This is accomplished by incorporating appropriate mechanisms within the pump itself.

16 Claims, 30 Drawing Sheets

U.S. PATENT DOCUMENTS

| | | |
|---|---|---|
| 4,407,278 A | 10/1983 | Burton et al. |
| 4,412,530 A | 11/1983 | Burton |
| 4,437,457 A * | 3/1984 | Trick et al. .................... 600/31 |
| 4,453,536 A | 6/1984 | Abild |
| 4,489,732 A | 12/1984 | Hasson |
| 4,537,183 A | 8/1985 | Fogarty |
| 4,553,959 A | 11/1985 | Hickey et al. |
| 4,566,446 A | 1/1986 | Fogarty |
| 4,571,241 A | 2/1986 | Christopher |
| 4,590,927 A | 5/1986 | Porter et al. |
| 4,632,435 A | 12/1986 | Polyak |
| 4,671,261 A | 6/1987 | Fischell |
| 4,682,583 A * | 7/1987 | Burton et al. .................. 600/31 |
| 4,710,169 A | 12/1987 | Christopher |
| 4,718,410 A | 1/1988 | Hakky |
| 4,782,826 A | 11/1988 | Fogarty |
| 4,850,963 A | 7/1989 | Sparks et al. |
| 4,932,938 A | 6/1990 | Goldberg et al. |
| 4,944,732 A | 7/1990 | Russo |
| 4,958,630 A | 9/1990 | Rosenbluth et al. |
| 4,968,294 A | 11/1990 | Salama |
| 5,030,199 A | 7/1991 | Barwick et al. |
| 5,034,009 A | 7/1991 | Mouchel |
| 5,041,092 A | 8/1991 | Barwick |
| 5,048,510 A | 9/1991 | Hauschild et al. |
| 5,048,511 A | 9/1991 | Rosenbluth et al. |
| 5,062,417 A | 11/1991 | Cowen |
| 5,063,914 A | 11/1991 | Cowen |
| 5,074,849 A | 12/1991 | Sachse |
| 5,085,650 A | 2/1992 | Giglio |
| 5,088,980 A | 2/1992 | Leighton |
| 5,090,424 A | 2/1992 | Simon et al. |
| 5,112,295 A | 5/1992 | Zinner et al. |
| 5,114,398 A | 5/1992 | Trick et al. |
| 5,131,906 A | 7/1992 | Chen |
| 5,141,509 A * | 8/1992 | Burton et al. .................. 600/40 |
| 5,167,611 A | 12/1992 | Cowan |
| 5,171,272 A | 12/1992 | Levius |
| 5,186,180 A | 2/1993 | Bellas |
| 5,250,020 A | 10/1993 | Bley |
| 5,344,388 A * | 9/1994 | Maxwell et al. .............. 600/40 |
| 5,704,895 A * | 1/1998 | Scott et al. .................... 600/40 |
| 5,851,176 A | 12/1998 | Willard |
| 5,895,424 A | 4/1999 | Steele, Sr. et al. |
| 6,171,233 B1 | 1/2001 | Willard |

* cited by examiner

PRESSURE BASED SPONTANEOUS INFLATION INHIBITOR WITH PENILE PUMP IMPROVEMENTS

REFERENCE TO RELATED APPLICATIONS

This application is a continuation-in-part of U.S. patent application Ser. No. 09/749,292 entitled "PRESSURE BASED SPONTANEOUS INFLATION INHIBITOR" which was filed Dec. 27, 2000, now abandoned and claims the priority of provisional application Serial No. 60/295,326 entitled "PENILE PUMP IMPROVEMENTS" which was filed Jun. 1, 2001 (the entire contents of each of which are herein incorporated by reference).

BACKGROUND

This invention generally relates to a pump and valve assembly for inflating a prosthesis. More particularly, the invention relates to pressure based mechanisms that inhibit spontaneous inflation of the prosthesis, including stiffening and support mechanisms that also improve the function of the valve.

One common treatment for male erectile dysfunction is the implantation of a penile prosthesis. Such a prosthesis typically includes a pair of inflatable cylinders which are fluidly connected to a fluid (typically liquid) reservoir via a pump and valve assembly. The two cylinders are normally implanted into the corpus cavernosae of the patient and the reservoir is typically implanted in the patient's abdomen. The pump assembly is implanted in the scrotum. During use, the patient actuates the pump and fluid is transferred from the reservoir through the pump and into the cylinders. This results in the inflation of the cylinders and thereby produces the desired penis rigidity for a normal erection. Then, when the patient desires to deflate the cylinders, a valve assembly within the pump is actuated in a manner such that the fluid in the cylinders is released back into the reservoir. This deflation then returns the penis to a flaccid state.

With inflatable penile prostheses of current designs, spontaneous inflation of the cylinders is known to occasionally occur due to inadvertent compression of the reservoir, resulting in the undesired introduction of fluid into the cylinders. Such inadvertent inflation can be uncomfortable and embarrassing for the patient. This undesirable condition is further described below with reference to a particular prosthetic design.

With reference to FIG. 1, a known pump and valve assembly 8 for use in a penile prosthesis includes a fluid input 10 that is coupled at one end to a reservoir (not shown) and to a housing 12 at its opposite end. Also connected to the housing 12 is a fluid output 14 which, in turn, is connected at its other end to a pair of cylinders (not shown). Linking the fluid input 10 and the fluid output 14 to each other is a common passageway 33, which itself contains a valve assembly that is described in greater detail below. Common passageway 33 is also in fluid communication with a pump bulb 18 that is used to move fluid from the reservoir (not shown) to the cylinders (not shown) in order to inflate the cylinders. The valve assembly located within common passageway 33 includes a reservoir poppet 20 which is biased against a valve seat 24 by a spring 28 and a cylinder poppet 22 which is biased against a valve seat 26 by a spring 30. The springs 28 and 30 are sized so as to keep the reservoir poppet 20 and the cylinder poppet 22 biased against each respective valve seat 24 and 26 under the loads that are encountered when the reservoir is pressurized to typical abdominal pressures.

When the patient wishes to inflate the cylinders, pump bulb 18 is squeezed so as to force fluid from the pump bulb 18 into the common passageway 33. The resulting fluid flow serves to reinforce the force from the spring 28 urging the reservoir poppet 20 against valve seat 24 while at the same time causing compression of the spring 30, and thereby opening cylinder poppet 22. As a result, the fluid travels out through fluid output 14 and into the respective cylinders.

When the patient releases the pump bulb 18 a vacuum is created, thus pulling the poppet 22 back against valve seat 26 (aided by spring 30) and simultaneously pulling the reservoir poppet 20 away from its valve seat 24, against the spring 28. As a result, fluid from the reservoir is thus allowed to flow through the fluid input 10 and into the common passageway 33 passing around the reservoir poppet 20 and into the vacuous pump bulb 18. Once the pump bulb 18 has been filled, the negative pressure is eliminated and the reservoir poppet 20 returns to its normal position. This pumping action of the pump bulb 18 and valve assembly is repeated until the cylinders are fully inflated.

To deflate the cylinders, the patient grips the housing 12 and compresses it along the axis of reservoir poppet 20 and cylinder poppet 22 in a manner such that the wall 13 of the housing 12 contacts the protruding end 21 of the reservoir poppet 20 and forces the reservoir poppet 20 away from valve seat 24. This movement, in turn, causes the reservoir poppet 20 to contact cylinder poppet 22 and force cylinder poppet 22 away from valve seat 26. As a result, both poppets 20 and 22 are moved away from their valve seats 24 and 26 and fluid moves out of the cylinders, through the fluid output 14, through common passageway 33, through the fluid input 10 and back into the reservoir.

Although the springs 28 and 30 are sized to provide sufficient tension to keep poppets 20 and 22 firmly abutted against valve seats 24 and 26 under normal reservoir pressures, it is possible that pressure that exceeds the force provided by the springs could be exerted upon the reservoir during heightened physical activity or movement by the patient. Such excessive pressure on the reservoir may overcome the resistance of the spring-biased poppets 20 and 22 and thereby cause a spontaneous inflation of the cylinders. After implantation, encapsulation or calcification of the reservoir may occur. Encapsulation or calcification of the reservoir can lead to additional problems. In particular, the encapsulation could lead to a more snugly enclosed reservoir, thus increasing the likelihood of spontaneous inflation.

In previous attempts to reduce or eliminate the occurrence of spontaneous inflation, different types of spontaneous inflation preventing valves have been introduced into the pump and valve assembly. Such previous valves are intended to permit the positive flow of fluid to the cylinders only in those circumstances when the patient has forcibly manipulated the valve.

Although such previous valve designs reduce the frequency of spontaneous inflation, several drawbacks do exist. For example, such valves are typically complex, requiring two-handed operation which is a serious drawback to elderly or severely ill patients. Some spontaneous inflation preventing valves also require the application of excessive force in order to manipulate the valves; which may be too demanding for some patients. Furthermore, such valve designs may cause patient discomfort due to the valve size or shape, because of increase in the overall volume of the implant within the patient. This increased size can also lead to interference with the patient's normal bodily functions. Such previous valve designs typically add undesirable cost to the device as well as increase the complexity of the surgical implantation procedure.

A solution to the above-identified drawbacks is disclosed in co-pending U.S. patent application Ser. No. 09/749,292 entitled "PRESSURE BASED SPONTANEOUS INFLATION INHIBITOR" which is assigned to the Assignee of the present invention and is incorporated herein by reference. However, the operational efficiency of the prosthesis pump could be further improved by optimizing the operative manipulation of the assembly.

Presently, the pump and valve assemblies used in implantable prostheses share certain characteristics. A compressible pump bulb is attached to the housing and is in fluid communication with the various fluid pathways. In order to inflate the cylinders, the compressible pump bulb is actuated by the patient, thereby urging fluid past the poppets into the cylinders. In order to deflate the cylinders, the valve housing is grasped and squeezed (through the patient's tissue), causing the poppets to unseat and allow fluid to flow back to the reservoir.

Since the pump and valve assembly is positioned within the patient's scrotum, the various components of the assembly must be small. As a result, manipulation of the pump and valve assembly is sometimes difficult. For example, patients requiring the use of a penile prosthesis are oftentimes elderly and have a reduced dexterity as a result of aging. Thus, in some instances, even locating the device within the tissue can be a challenge, let alone identifying the correct portion of the assembly to actuate. More specifically, with some patients it may be difficult to determine whether the housing portion of the assembly that leads to release or deflation of the cylinders is being grasped, or whether the bulb portion which would be used to inflate the cylinders is being grasped.

Notably, the length of the valve assembly is determined (at least in one direction) by the size of the various poppets and the distance such poppets must move in order to open and close the various fluid passageways. As a result, such a pump and valve assembly typically is longer in a direction parallel with the poppets. Moreover, in order to release the poppets in an assembly configured in this manner, the patient must grasp the narrower, shorter sidewalls of the assembly and compresses them together. Such a configuration can present challenges insofar as the spring tension of the poppets at the time of desired deflation is typically at a maximum while the surface area of the assembly which must be compressed in order to cause such deflation is at a minimum. This condition can lead to a situation where the patient has difficulty actually compressing the assembly, or in extreme circumstances, actually loses grip of the assembly during such attempts at deflation.

There exists a need for an improved prosthetic penile implant having a spontaneous inflation prevention mechanism that affords convenient operative manipulation by a patient.

SUMMARY OF THE INVENTION

The present invention includes a penile pump having a dual poppet arrangement wherein the poppets act as check valves or flow valves. Each poppet is spring-biased against a valve seat, and under normal circumstances, only allows positive fluid flow when a pump bulb is operated, thus causing an increase in fluid pressure which is transferred to the inflatable cylinders. To prevent spontaneous inflation when an overpressurization occurs in the reservoir, the same reservoir pressure is utilized to seal the fluid output against itself or to seal one or both of the poppets against the valve seat. Thus, the fluid is prevented from reaching the cylinders and creating a spontaneous inflation. When the movement or activity generating the overpressure in the reservoir is released, the system should return to equilibrium. Even if overpressurization of the reservoir is occurring, the pressure generated by compressing the pump bulb will far exceed the level of overpressure. Thus, the poppets will open in the normal way, allowing fluid to flow to the cylinders. The use of the overpressure in the reservoir itself to prevent fluid flow to the cylinders can occur in a variety of formats.

In still another embodiment, the reservoir poppet is actually coupled to an outer wall defining a portion of the fluid input. When an overpressurization in the reservoir occurs, this outer wall is forced to expand which simultaneously causes the reservoir poppet to be pulled firmly against the valve seat. This effectively prevents fluid flow from reaching the cylinders and causing a spontaneous inflation.

In yet another embodiment of the present invention, the valve seat is provided with a flexible valve which cooperates with the first poppet to prevent spontaneous inflation which could be caused by excessive pressure in the reservoir. Specifically, pressure in the reservoir and associated valve input is presented to the flexible valve and thus causing the valve to be further forced against the poppet, thus sealing off the input. When inflation is desired however, the negative pressure pulling the first poppet away from the valve seat will allow the desired fluid flow.

In yet still another embodiment, a tapered poppet is utilized in conjunction with a tapered valve seat. Each of these tapers do not exactly match each other, thus providing variable reactions to pressure signals.

In a further embodiment, a section of the reservoir poppet protrudes into the reservoir chamber. This protruding section of the reservoir poppet is coupled to the outer wall of the reservoir chamber. The poppet is coupled to the wall with a connecting spring that permits relative movement between the poppet and the outer wall. The tension of the spring is selected so that it approximates the forces generated by pressurized fluid acting on the wall of the reservoir chamber. However, the spring force is not so great as to prevent the vacuum generated by the pump bulb from opening the poppet. Thus, when the pump bulb is compressed and released, the vacuum forces generated are sufficient to unseat to the reservoir poppet despite its connection to the outer reservoir chamber wall.

In yet still a further embodiment, a relatively large and powerful biasing spring is coupled with the reservoir poppet to exert a relatively large force against the reservoir poppet forcing it into a sealing or closed position. Due to the strong biasing forces of the spring, overpressurization forces generated in the reservoir chamber are insufficient to unseat the reservoir poppet. Simply using such a spring will make it difficult for the vacuum forces generated by compression of the pump bulb to unseat the reservoir poppet. To eliminate this problem, the face of the reservoir poppet, which forms a fluid-tight seal when the reservoir poppet is in a closed position, is made relatively large. That is, the diameter of the face approaches the diameter of the chamber containing the reservoir poppet. Thus, the vacuum forces generated will act over a larger surface area thereby exerting a larger degree of force, which permits the unseating of the reservoir poppet despite the opposing force of the biasing spring.

Because it is difficult to fabricate a housing having a planar wall that interacts with the planar poppet face to form a sufficiently fluid-tight seal, the portion of the housing holding the reservoir poppet contains a pair of spaced lip seals. The position of the lip seal serves two distinct purposes. The first is to prevent fluid pressure generated during over pressurization of the reservoir from engaging a large portion of the poppet face, which would in effect defeat the added strength provided by the biasing spring. The outer seal is also provided so that when a vacuum force is generated, the vacuum cannot act on the front surface of the poppet face which would, in effect, hold the reservoir poppet in a closed position.

In another embodiment of the present invention, the reservoir poppet is configured with a throughbore at a rear portion of the reservoir poppet that is in fluid communication with a passageway and an outlet adjacent to the cylinder poppet. A sliding valve seal is positioned over this section of the reservoir poppet. The sliding valve seal is held against the back wall of the chamber by a spring positioned between the front face of the sliding valve seal and the back face of the suction poppet valve seal. The arrangement of the valve sleeve on the rear of the reservoir poppet is such that fluid is only able to flow through the throughbore and out of the outlet when the valve sleeve is positioned near the rear of the chamber and the front face of the reservoir poppet is firmly seated. In a reservoir overpressurization situation, the valve sleeve is again pressed against the rear of the chamber. However, the reservoir poppet is also forced backwards into the chamber, forcing the throughbore to be occluded by the valve sleeve. This prevents fluid from flowing towards the cylinder poppet which could ultimately lead to spontaneous inflation.

In yet another embodiment, the portion of the housing between the cylinder poppet and the reservoir chamber has been modified. In addition, the reservoir poppet is provided with a unique configuration to interact with the housing structure. The reservoir poppet has a face, similar to the other embodiments, that is spring biased towards a matching valve seat. An annular ring is molded into the housing just behind (towards the cylinder poppet) the valve seat and is sized to interact with the face.

The pump assembly of this embodiment has two states, activated and deactivated. In the activated state, the reservoir poppet is positioned so that the face is between the annular ring and the valve seat. When so positioned, the pump assembly functions as previously described with reference to the other embodiments. A compression of the pump bulb force the face against the valve seat and causes the cylinder poppet to open. A release of the pump bulb generates a vacuum which removes the reservoir poppet face from the valve seat and allows fluid to flow from the reservoir and into the pump bulb. Thus, the activated state is used when actively inflating the cylinders and while it is desired to maintain the cylinders in an inflated state.

In the deactivated state, the reservoir poppet is positioned so that the face moves through the annular ring. In this position, the face will be between the cylinder poppet and the annular ring and the reservoir poppet spring will bias the face so that it abuts the annular ring. In other words, the face is displaced from the valve seat, and a gap exists between the valve seat and the annular ring. The stem of the reservoir poppet extends from the face towards the cylinder poppet. The stem is a cylindrical member having a generally V-shaped groove extending about its circumference near the middle of the stem. The stem interacts with a flexible conical lip seal molded within the housing. When in the activated state, the conical lip seal is positioned near the V-shaped groove so that fluid flow is essentially unhindered. When in the deactivated state, the conical lip seal is caused to engage the cylindrical portion of the stem. Thus, a fluid tight seal can be formed.

When in the deactivated state, the reservoir poppet can be moved to engage and release the cylinder poppet, leading to a deflation of the cylinders. During this time, the conical lip seal continues to be located near the cylindrical portion of the stem; however, the flexible nature of the conical lip seal allows fluid flow in a direction from the cylinders to the reservoir. The pump assembly must be placed in the deactivated state to prevent spontaneous inflation. When in this state, the conical lip seal engages the cylindrical portion of the stem. If overpressure is generated, the reservoir poppet can be displaced towards the cylinder poppet. As this occurs, the increased fluid pressure levels force the conical lip seal to firmly abut the cylindrical portion of the stem, preventing increased pressure levels from reaching and displacing the cylinder poppet. Thus, spontaneous inflation is prevented.

To further improve the operational efficiency of the pump and valve assembly, in yet still another embodiment, a reservoir poppet is made of a metal material with a plastic member disposed over a segment of the metal material. The plastic segment of the reservoir poppet prevents undesired frictional contact (metal on metal) with other metal members, and prevents premature wearing of the contact point of the two components.

In another embodiment, a pump and valve assembly includes a pump bulb that is differentiated from the valve housing when inflation of the cylinders is desired. To supplement differentiation between the bulb and the valve housing, the valve housing is provided with a textured surface so that even through tissue the patient is able to readily discern which area comprises the pump bulb and which area comprises the valve housing. This is important in that the pump bulb is compressed for inflation while the valve housing is compressed for deflation.

The pump assembly is configured such that it has a length longer than its width, with its internal poppets running parallel with the length. To release fluid from the inflated cylinders, the internal poppets are actuated so that they move in a direction parallel to the length, until they open. To achieve this action directly, the opposing sides of the width of the valve housing are compressed. This compression causes actuation of the internal poppets.

In addition, an actuating bar is positioned within the valve housing parallel with and extending along at least one of the sides of the length. An arm attached to the actuating bar extends along a portion of one of the sides of the width in close proximity to the tip of one of the poppets. Thus, the configuration of the actuating bar causes it to engage and open the poppet allowing fluid to flow from the cylinder to the reservoir. Furthermore, the patient can grasp the valve housing in virtually any orientation and when pressure is applied, the actuating bar will act either directly or indirectly to open the appropriate poppets. Thus, so long as the patient grasps any portion of the pump and valve assembly other than the pump bulb, compression will result in the desired opening of the poppets which allows the cylinders to deflate.

Furthermore, since the patient can grasp the valve housing along the sides of the length, i.e., surfaces with larger surface area, less pressure need be applied to achieve the successful opening of the poppets. In other words, by increasing the surface area that is engaged by the patient's fingers and appropriately positioning the actuating bar, less force need be exerted by the patient to achieve the desired result.

The textured surface of the valve housing not only helps the patient identify the correct portion of the pump and valve assembly to actuate, it also serves to prevent slippage once the patient begins to compress the housing. Thus, what is achieved is an efficient and ergonomic pump and valve assembly for an implantable prosthesis. The pump and valve assembly can advantageously be formed from a minimal number of components. That is, all that need be molded are a valve block and a corresponding pump bulb which surrounds the valve block. The various poppets can be inserted into the valve block and then placed within the interior of the pump bulb, thus forming a completed assembly. This results in certain manufacturing efficiencies, thus reducing both cost and time of production.

To prolong the life of the valve assembly, ribs are added to the actuating bar. The ribs increase the strength and stiffness of the actuating bar and prevent deflection during actuation. Permanent deformation of the actuating bar is prevented when normal deflection occurs during actuation. As a result, full axial motion of the poppet is ensured. Another rib is disposed along an actuation face of the actuating bar to also limit deformation during actuation.

To improve the ease of deflation, a stiff poppet support wraps around the valve body and rests against a portion of the check valve. The poppet support has a shelf that provides a smooth surface for a portion of the check valve to slide. The poppet support contacts the check valve and prevents undesirable sideways movement of the check valve against the valve body. The positioning and configuration of the poppet support thus allows the check valve to easily move axially into the valve body to an open position. This results in improved operational efficiency of the prosthesis pump and an extended operating life.

In most of the embodiments, the force generated by an overpressurization of the reservoir is used to prevent fluid flow into the cylinders.

DETAILED DESCRIPTION OF PREFERRED EMBODIMENTS

Figure 1:
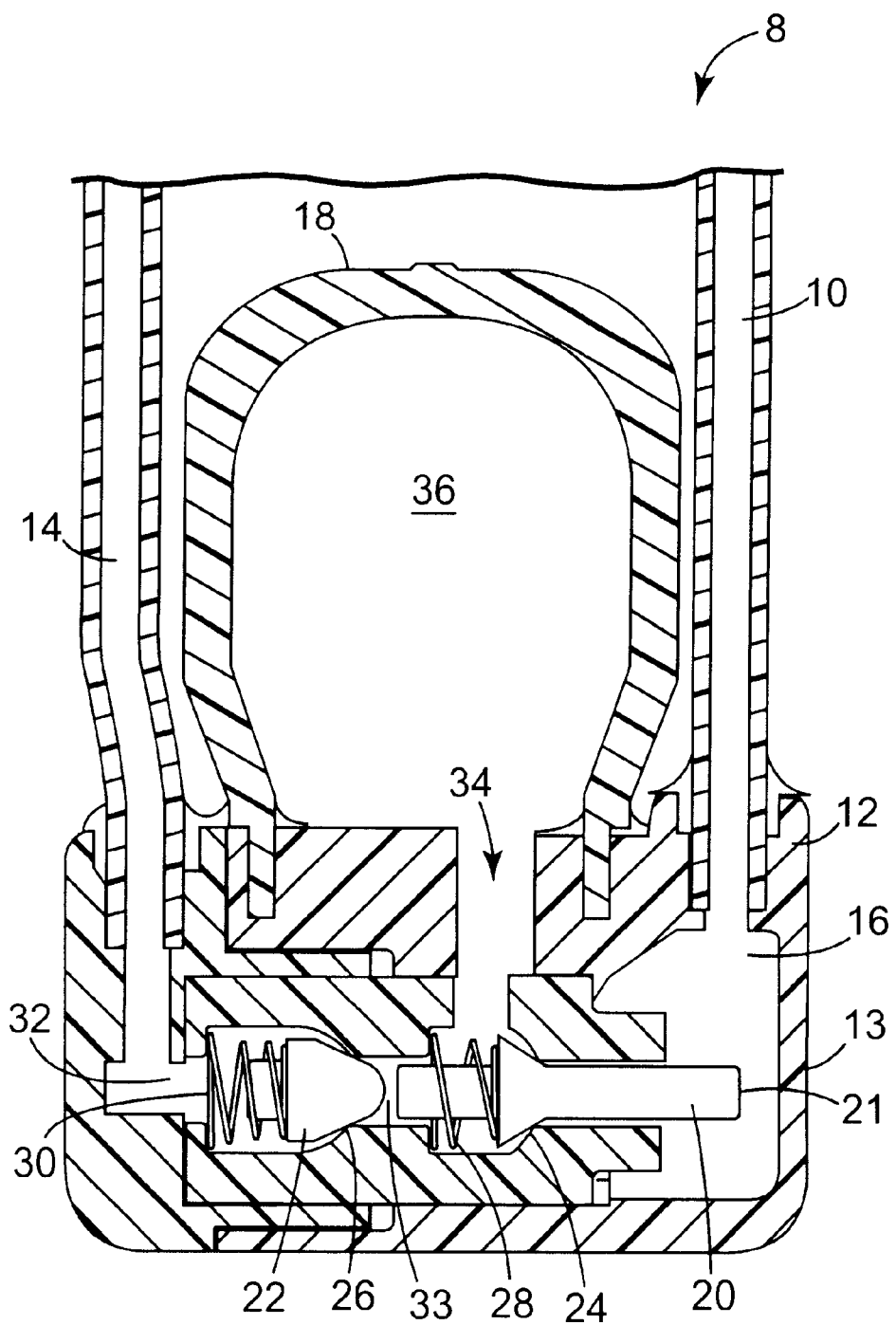
FIG. 1 is a side-sectional view of a penile pump according to the teachings of the prior art.

Referring to FIG. 1, a pump assembly is shown and generally referred to as 8. The pump assembly 8, as illustrated in FIG. 1, is essentially that of the prior art, but an understanding of the working elements of pump assembly 8, as illustrated in FIG. 1, is beneficial to understanding the operation of each embodiment of the present invention. Generally, the pump assembly 8 will be implanted into the patient's scrotum. A separate fluid-filled reservoir (not shown) is implanted in some other portion of the patient's body, usually in the abdomen. Fluidly connecting the reservoir to the pump assembly 8 is fluid input 10 which will usually be a flexible silicone tube. A pair of inflatable cylinders (not shown) are usually implanted in the patient's corpus cavernosae and are fluidly connected to pump assembly 8 via fluid output 14, which is also usually a flexible silicone tube.

In general, when pump assembly 8 is actuated, fluid is drawn from the reservoir through the pump assembly 8 and pumped into the cylinders. During the inflation process and until released by the patient, the pump assembly 8 maintains the fluid pressure in the cylinders, thus keeping them in their inflated state. When deflation is desired, the patient manipulates assembly 8, permitting fluid to transfer out of the inflatable cylinders and into the reservoir, thereby deflating the cylinders and returning them to a flaccid state.

Pump assembly 8 generally includes a housing 12 usually formed of silicone. Attached to housing 12 is a pump bulb 18, which includes a relatively large pump chamber 36. Fluid input 10 is coupled to the housing 12 and empties into a reservoir chamber 16. As such, fluid input 10 couples reservoir chamber 16 to the reservoir. A common passageway 33 is fluidly coupled to reservoir chamber 16 at one end of the housing 12, and is fluidly coupled to fluid output 14 at an opposite end of the housing 12. Similarly, the pump chamber 36 is fluidly coupled to the common passageway 33 via pump passageway 34.

Disposed within common passageway 33 is a reservoir poppet 20 which functions as a check valve. Reservoir poppet 20 is an elongated member having a contoured portion which abuts reservoir poppet valve seat 24 forming a fluid tight seal. A reservoir poppet spring 28 engages reservoir poppet 20 and biases reservoir poppet 20 against the reservoir poppet valve seat 24. Also disposed within common passageway 33 and in line with reservoir poppet 20 is cylinder poppet 22. Cylinder poppet 22 forms a second check valve within common passageway 33. Cylinder poppet 22 is biased by cylinder poppet spring 30 against cylinder poppet valve seat 26 in a normal state, thereby forming another fluid tight seal within common passageway 33. Reservoir poppet 20 is substantially longer than cylinder poppet 22. A front end of reservoir poppet 20 extends into reservoir chamber 16, in close proximity to an outer wall of housing 12. Furthermore, the front end of cylinder poppet 22 is in close proximity to the rear end of reservoir poppet 20. As such, the patient can manipulate both poppets 20 and 22 by compressing the wall of housing 12. Compression of the housing 12 will cause the reservoir poppet 20 to compress reservoir poppet spring 28 thus displacing the reservoir poppet 20 from reservoir poppet valve seat 24. This motion will also cause cylinder poppet 22 to be displaced from cylinder poppet valve seat 26 while compressing cylinder poppet spring 30. When both reservoir poppet 20 and cylinder poppet 22 are displaced from their respective valve seats, fluid is allowed to freely flow between reservoir chamber 16 and fluid output 14, and hence fluid is allowed to freely flow between the reservoir and the cylinders.

During a majority of the time, pump assembly 8 will be in the configuration shown in FIG. 1. That is, both reservoir poppet 20 and cylinder poppet 22 are abutting their respective valve seats 24 and 26, forming a fluid tight seal. When inflation is desired, pump bulb 18 is manually compressed by the patient. This forces the fluid in pump chamber 36 out through pump passageway 34 and into common passageway 33, under relatively high pressure. Because of the location of pump passageway 34 with respect to the reservoir poppet 20, this increased pressure causes reservoir poppet 20 to further abut reservoir poppet valve seat 24. This increased pressure is more than sufficient to remove cylinder poppet 22 from its abutment with cylinder poppet valve seat 26, by compressing cylinder poppet spring 30. As such, the pressurized fluid is allowed to pass through a portion of the common passageway 33 and into fluid output 14, where it eventually reaches an inflatable cylinder. When released, the pump bulb 18 expands back to its original configuration, creating negative pressure within pump chamber 36 and common passageway 33. This negative pressure draws cylinder poppet 22 towards valve seat 26 and simultaneously pulls reservoir poppet 20 away from valve seat 24. As such, fluid is drawn from the reservoir and into pump chamber 36 until the negative pressure is eliminated. Then, reservoir poppet spring 28 causes the reservoir poppet 20 to reseat itself against valve seat 24.

Repeated compression of pump bulb 18 eventually inflates the cylinders to a sufficient degree of rigidity for the patient. Once inflated, the fluid remaining in fluid output 14 is under a relatively high degree of pressure. This high pressure fluid aids cylinder poppet spring 30 in forcing cylinder poppet 22 against cylinder poppet valve seat 26 again forming a fluid tight seal and preventing fluid from within the cylinders from passing through (preventing deflation of the cylinders).

When the patient desires deflation of the cylinders, the wall of housing 13 is manually compressed. This compression forces reservoir poppet 20 away from reservoir poppet valve seat 24 and simultaneously causes cylinder poppet 22 to be removed from cylinder poppet valve seat 26. The pressurized fluid within the cylinders and fluid output 14 naturally returns to the reservoir via common passageway 33. Furthermore, the cylinders can be manually compressed forcing out any remaining fluid. Once the cylinders are satisfactorily emptied, the patient releases the grip on housing 12, thus allowing cylinder poppet 22 and reservoir poppet 20 to once again abut their respective valve seats 24 and 26.

As described above, pump assembly 8 (as shown in FIG. 1) works relatively well under normal circumstances. However, when the patient compresses the reservoir inadvertently through bodily movement, the pressure generated may be sufficient to remove reservoir poppet 20 and cylinder poppet 22 from their respective valve seats 24 and 26, thus spontaneously inflating the cylinders. When sufficient force is generated against the reservoir (or a similar component) to cause the fluid pressure to exceed the resistive characteristics of poppets 20 or 22, an overpressure situation has occurred. Of course, the only way to release this spontaneous inflation is to manually release the check valves.

To date, it has been very difficult to monitor and determine the pressures generated in an overpressure situation since each patient exhibits unique individual characteristics. Furthermore, each spontaneous inflation may result from a very different physical act on the part of the patient. However, it appears that pressure generated by compression of the reservoir results in a fluid pressure of up to 3 pounds per square inch (1.361 kg/25.4$^2$ mm) but may be as high as 6–8 pounds per square inch (2.722 kg/25.4$^2$ mm). Conversely, compression of the pump bulb 18 will usually generate pressures on the order of 20 pounds per square inch (9.072 kg/25.4² mm).

Figure 2:
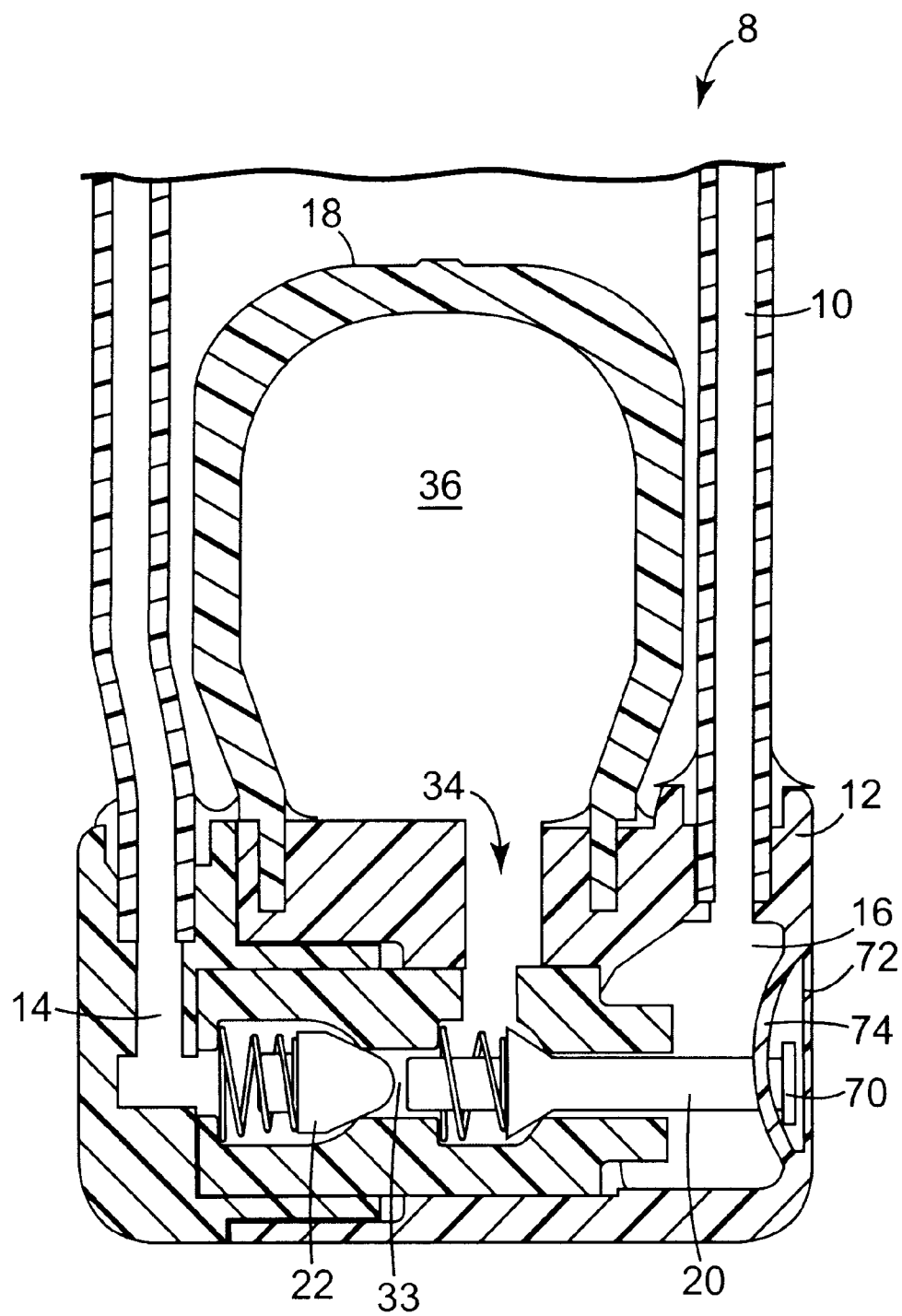
FIG. 2 is a side-sectional view of a penile pump wherein the reservoir poppet has been attached to an outer wall of the reservoir chamber.

Referring to FIG. 2, a first embodiment of the present invention is illustrated. A fluid input 10 couples a reservoir to reservoir chamber 16. Reservoir poppet 20 has been modified to include a T-shaped tip 70. Tip 70 is secured to an outer reservoir chamber wall 72. Tip 70 is secured to the outer reservoir chamber wall by one or more connecting bands 74. Sufficient freedom of movement for reservoir poppet 20 is provided so that during normal operation reservoir poppet 20 can be dislodged from its abutment with reservoir poppet valve seat 24.

During an overpressure situation, the reservoir is compressed, pressurizing the fluid and directing it through fluid input 10 and into reservoir chamber 16. Outer reservoir chamber wall 72 has been made sufficiently flexible so that when this occurs, reservoir chamber 16 is caused to expand due to the increased pressure generated. As outer reservoir chamber wall 72 expands, connecting bands 74 coupled with tip 70 pull reservoir poppet 20 tightly against reservoir poppet seat 24. The overpressurization generated by the reservoir is used against itself to prevent fluid from reaching the cylinders and creating a spontaneous inflation.

Figure 3:
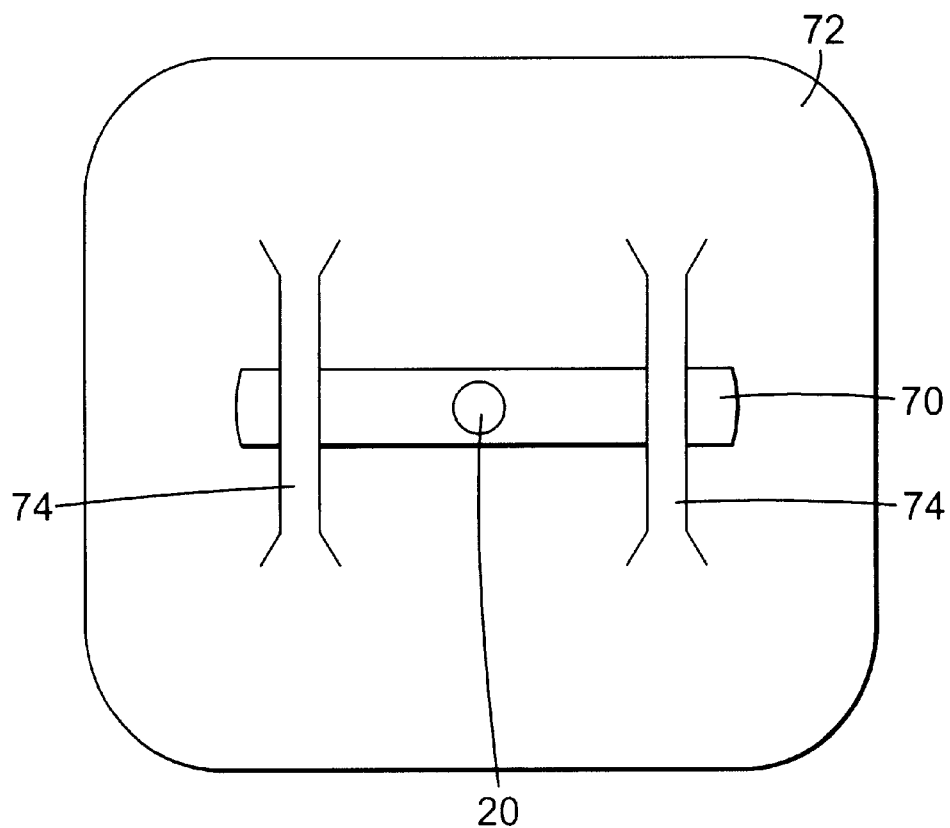
FIG. 3 is a side, partially sectional planar view of the attachment mechanism connecting the reservoir poppet to the outer wall of the fluid input chamber.

Referring to FIG. 3 a side partially sectional view is shown which helps illustrate the interior side of outer reservoir chamber wall 72. Tip 70 of reservoir poppet 20 is secured at each end by a connecting band 74 which overlaps tip 70 and is interconnected with outer reservoir chamber wall 72. Any interconnection of tip 70 or reservoir poppet 20 to outer reservoir chamber wall 72 is acceptable so long as during an overpressurization situation, reservoir poppet 20 is pulled against reservoir poppet valve seat 24 and during normal use sufficient flexibility is provided so that reservoir poppet 20 can be displaced from reservoir poppet valve seat 24 allowing the desired fluid flow.

Figure 4:
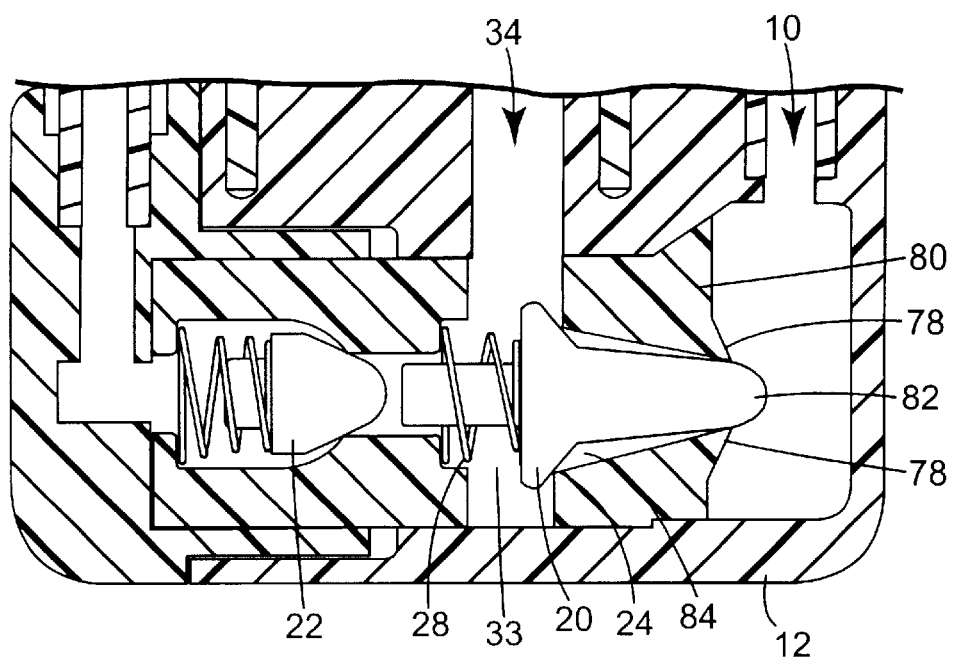
FIG. 4 is a side sectional view of housing for a penile pump having a tapered reservoir poppet and corresponding passageway which plugs the fluid input during overpressure situation.

Referring to FIG. 4, a second embodiment of the present invention is illustrated. FIG. 4 illustrates the portion of housing 12 containing reservoir poppet 20 and cylinder poppet 22. Reservoir poppet 20 is an elongated member that terminates in a nose 82. A tapered reservoir passageway 84 is provided through a sidewall 80 located adjacent to fluid input 10. Located at the junction of the sidewall 80 and reservoir passageway 84 is a flap 78 that is able to flex, with respect to sidewall 80. Flap 78 is simply the terminus of sidewall 80 at the passageway 84, and will optimally be offset by some angle from the remainder of the sidewall 80.

As illustrated in FIG. 4, reservoir poppet 20 is in a sealed position. That is, fluid is not able to pass from fluid input 10 through tapered passageway 84 and beyond, because reservoir poppet 20 is sealed against sidewall 80 at reservoir poppet valve seat 24 and is held in place by spring 28. In addition, nose 82 of reservoir poppet 20 contacts flap 78, providing a further seal. The remainder of passageway 84 is open between reservoir poppet 20 and sidewall 80.

In normal use, reservoir poppet 20 is pulled away from its sealed position by a vacuum created at pump passageway 34. This allows fluid to pass from fluid input 10, through passageway 84, and then through common passageway 33 into pump bulb 18. During a compression of pump bulb 18, reservoir poppet 20 is further pressed against valve seat 24.

During an overpressure situation, the fluid pressure in the reservoir and hence within fluid input 10 will increase. This increased pressure is applied evenly within fluid input 10, however flaps 78 are able to give in response to these forces. As such, flap 78 will be forced against a portion of reservoir poppet 20. The shape of reservoir poppet 20 and passageway 84 are chosen so that as flap 78 is pressed against reservoir poppet 20, a strong seal is formed. In other words, sufficient give is provided in sidewall 80, particularly at and behind flap 78 (due to its shape and flexibility) so that increased pressure causes a fluid tight encasement of poppet 20 rather than a displacement of poppet 20. Therefore, reservoir poppet 20 remains sealed and spontaneous inflation is prevented. While one specific configuration of this concept is shown in FIG. 4, it is to be understood that a wide variety and combinations of the disclosed teachings may be used while achieving the same result. The shape of the reservoir poppet 20, passageway 84, and the location and shape of flap 78 are extremely variable so long as these elements work together to form a fluid tight seal during an overpressure situation.

Figure 5:
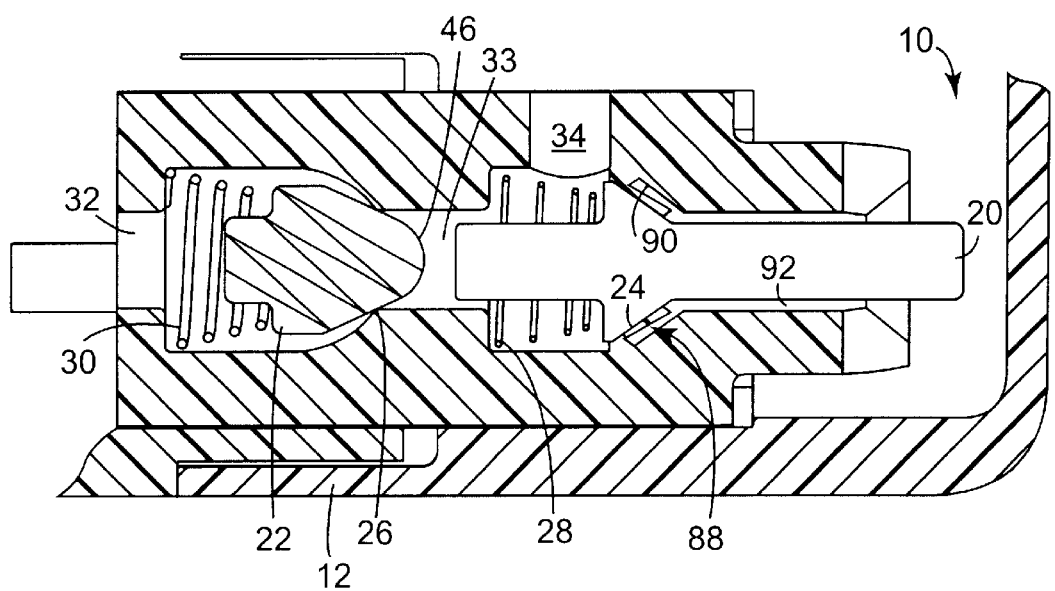
FIG. 5 is a side sectional view of housing for a penile pump having relief areas which expand during an overpressure situation and seal against the reservoir poppet.

Referring to FIG. 5, a third embodiment is illustrated. Reservoir poppet 20 is an elongated member that extends from common passageway 33, through poppet passageway 92 and into fluid input 10. As with many of the above embodiments, in one position the reservoir poppet 20 abuts reservoir poppet valve seat 24. Similarly, reservoir poppet 20 is only expected to be removed from valve seat 24 during a re-expansion of a compressed pump bulb 18. To prevent the removal of the reservoir poppet from valve seat 24 during an overpressure situation, relief area 90 has been formed within the housing 12. Formation of relief area 90 creates a flexible valve 88. Flexible valve 88 forms a part of the reservoir poppet valve seat 24, and appears as shown in FIG. 5, under normal circumstances.

Figure 6:
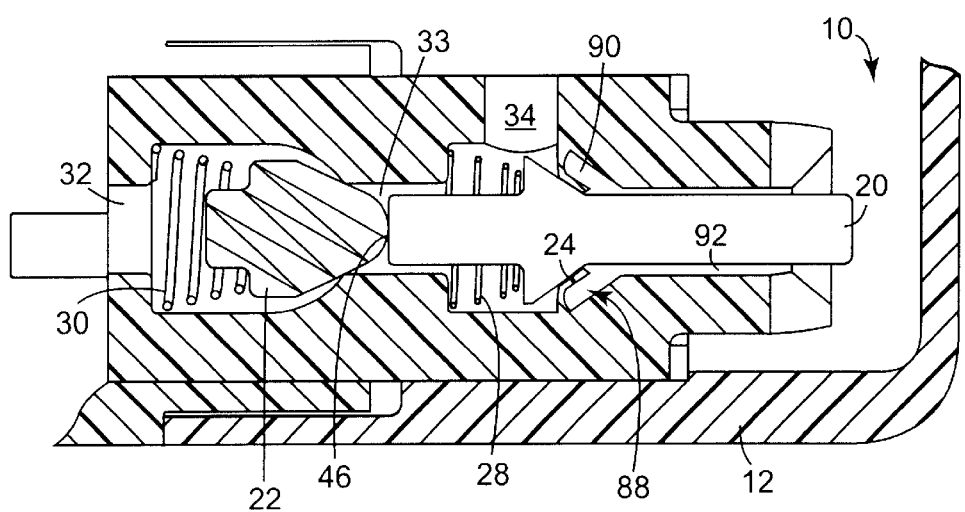
FIG. 6 is a side sectional view of the penile pump in FIG. 5, illustrated during an overpressure situation.

FIG. 6 illustrates an overpressure situation where the pressure of the fluid in fluid input 10 and poppet passageway 92 is relatively high. Rather than forcing reservoir poppet 20 from valve seat 24, this overpressure causes relief area 90 to expand; which in turn causes flexible valve 88 to even more firmly abut reservoir poppet 20. Depending upon the particular arrangement chosen, such an expansion of relief area 90 may cause some compression of reservoir poppet spring 28. In other words, reservoir poppet 20 is caused to move towards the cylinder poppet 22. Such motion will normally allow a spontaneous inflation to occur. However, in this embodiment, it is the movement of valve seat 24 that moves reservoir poppet 20, as such, a fluid seal is not only maintained, it is made stronger. To further support reservoir poppet 20, nose 46 of cylinder poppet is located in close proximity to the rear of reservoir poppet 20. As such, when expansion of relief area 90 causes a small amount of movement of reservoir poppet 20, reservoir poppet 20 is caused to abut cylinder poppet 22. Therefore, any further movement of reservoir poppet 20 requires compression of both reservoir poppet spring 28 and cylinder poppet spring 30. This combination of spring forces provides a relatively high resistive force opposing further movement of reservoir poppet 20, even during an overpressure situation. This combined with the expandable characteristics of relief area 90 prevents a spontaneous inflation from occurring. Of course, the relief area 90 can be fashioned to prevent such spontaneous inflation without causing the reservoir poppet 20 to engage cylinder poppet 22.

Figure 7:
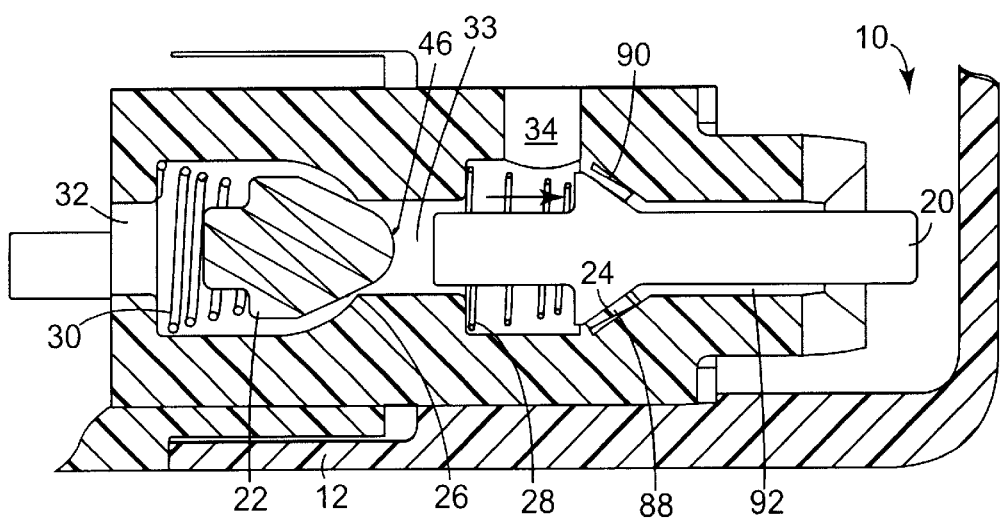
FIG. 7 is a side sectional view of the penile pump in FIG. 5, illustrated during a compression of the pump bulb.

FIG. 7 illustrates a state where pump bulb 18 is being compressed, forcing fluid around cylinder poppet 22 and out through cylinder poppet output 32. Simultaneously, reservoir poppet 20 is forced towards fluid input 10, causing flexible valve 88 to collapse against the inner portions of relief area 90. Once again, the strength of the seal at valve seat 24 is increased during such movement.

Figure 8:
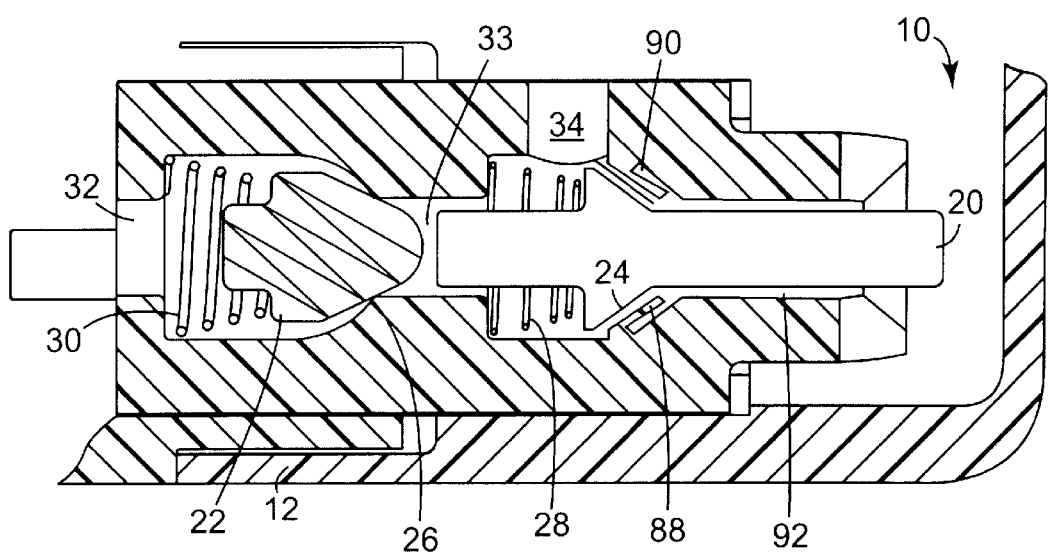
FIG. 8 is a side sectional view of the penile pump in FIG. 5, illustrated during a reinflation of the pump bulb.

Immediately after the state shown in FIG. 7 occurs, pump bulb 18 is released. As illustrated in FIG. 8, this creates a vacuum which pulls cylinder poppet 22 against cylinder poppet valve seat 26 and pulls reservoir poppet 20 away from valve seat 24; thus allowing fluid from the reservoir to flow into pump bulb 18. Flexible valve 88 is created with sufficient rigidity to resist being forced against reservoir poppet 20 while fluid is flowing through poppet passageway 92 and into pump bulb 18. Furthermore, the previous compression of flexible valve 88 against poppet 20 (FIG. 7) substantially evacuates relief area 90. Therefore when reservoir poppet 20 is initially pulled from valve seat 24, relief area 90 will remain in an evacuated state while fluid flow begins. The system is configured so that relief area 90 will not totally fill (and expand) with fluid and seal against reservoir poppet 20 until pump bulb 18 has been refilled. This can be done by making flexible valve 88 too rigid to allow such a seal to be formed in this state; providing for a sufficient amount of reservoir poppet 20 movement to prevent the flexible valve 88 from reaching poppet 20, even when relief area 90 is completely expanded; or simply imparting sufficient rigidity in flexible valve 88 so that the time is takes to expand relief area 90 is greater than the time it takes to refill pump bulb 18.

Figure 9:
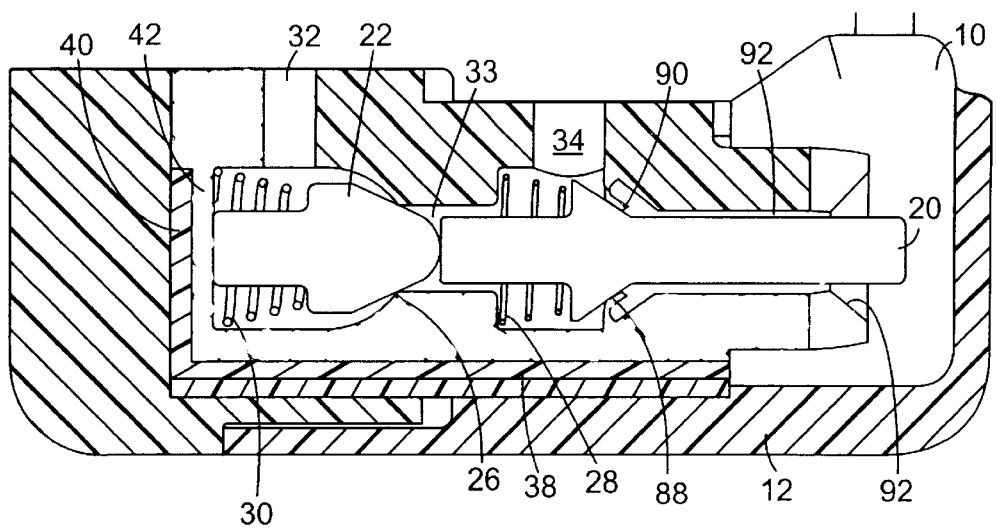
FIG. 9 is a side sectional view of the housing of a penile pump having relief areas which expand during an overpressure situation, and a termination chamber which cooperates with the cylinder poppet during the overpressure situation.

FIG. 9 illustrates a fourth embodiment utilizing a combined solution to avoid spontaneous inflation. Namely, relief area 90 has been provided and works as described above. In addition, bypass passageway 38 has been provided which fluidly connects fluid input 10 to termination chamber 40. Termination chamber 40 includes abutting wall 42, which acts as a diaphragm when an overpressure situation occurs. These two mechanisms will act in concert to prevent a spontaneous inflation from occurring. One advantage of this arrangement is that nose 46 of the cylinder poppet 22 will be displaced towards the rear of reservoir poppet 20 via an expansion of termination chamber 40. This force opposes the movement of the reservoir poppet 20, in the opposite direction that is generated from an expansion of relief area 90. In essence, the force generated by the overpressure is caused to directly oppose itself, which in turn prevents spontaneous inflation.

Figure 10:
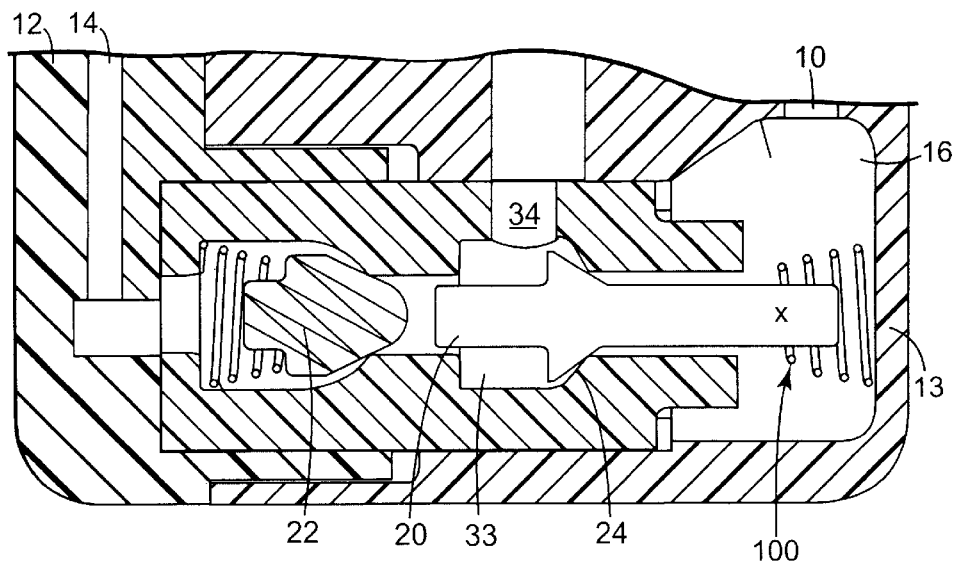
FIG. 10 is a side sectional view of a housing for a penile pump having a reservoir poppet coupled to the outer wall of the reservoir chamber via a connecting spring.

Referring to FIG. 10, a fifth embodiment to the present invention is illustrated. Housing 12 includes a fluid input 10 that is in fluid communication with fluid output 14 through a reservoir chamber 16 and a common passageway 33. Common passageway 33 is selectively occluded by a reservoir poppet 20 and cylinder poppet 22 which are both biased towards a closed position. A portion of reservoir poppet 20 is physically connected to a connection spring 100. The opposite end of connection spring 100 is attached to a wall 13 of housing 12. Connections to spring 100 are biased to maintain the configuration illustrated in FIG. 10.

Figure 11:
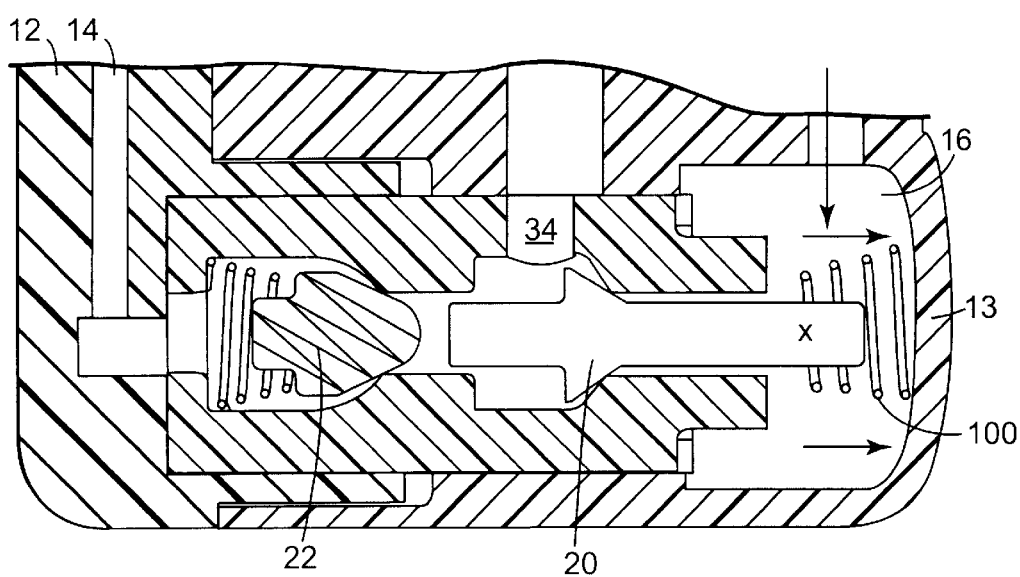
FIG. 11 is a side sectional view of the penile pump of FIG. 10 during an overpressurization situation.

FIG. 11 illustrates what occurs during an overpressurization situation. As increased fluid pressure is generated, wall 13 in reservoir chamber 16 is caused to expand outward as indicated by the arrows. Since connection spring 100 is fixedly attached to wall 13, the tension generated by expanding spring 100 serves to pull reservoir poppet 20 firmly against valve seat 24, creating an even more fluid tight seal.

Figure 12:
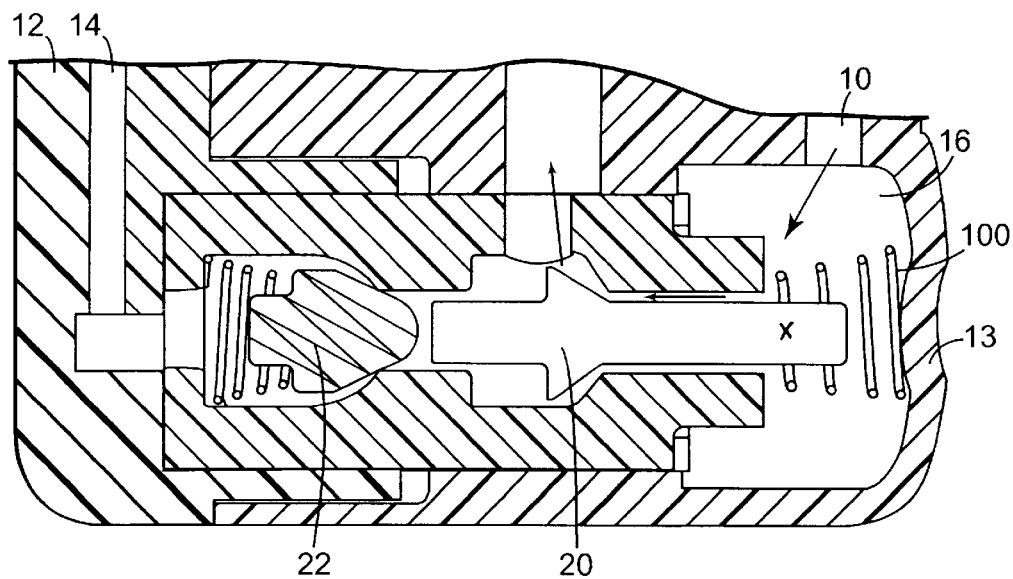
FIG. 12 is a side sectional view of the penile pump of FIG. 10 when vacuum forces are generated by the pump bulb.

Once pump bulb 18 has been compressed and released, vacuum forces are generated which unseat reservoir poppet 20. This situation is illustrated in FIG. 12. Thus, despite an overpressurization situation wherein wall 13 is expanded outwardly and connection spring 100 is pulling against reservoir poppet 20, the vacuum forces generated, are sufficient to unseat reservoir poppet 20 and allow fluid flow into pump bulb 18 (as shown by flow arrows A).

Figure 13:
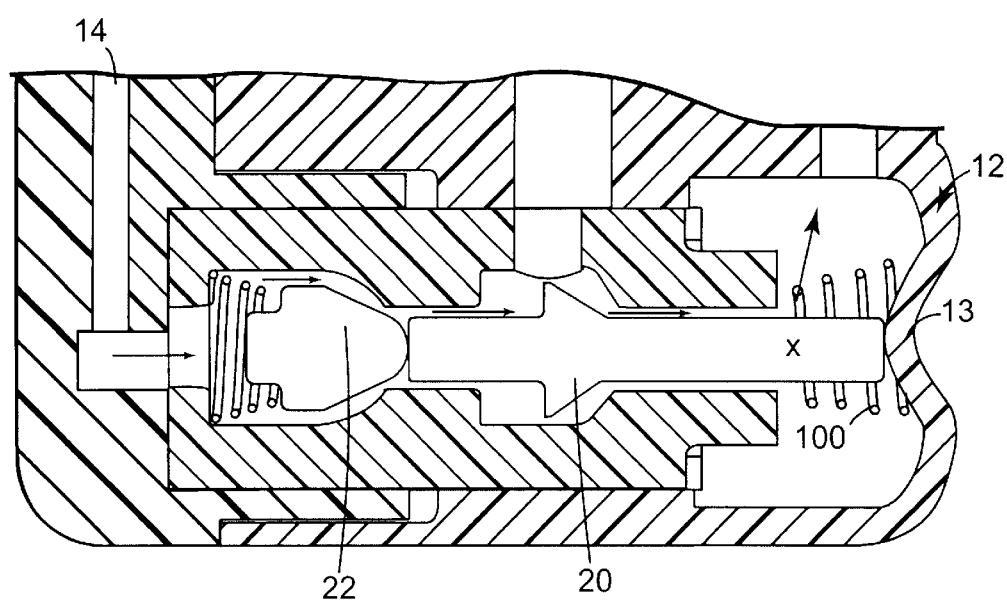
FIG. 13 is a side sectional view of the penile pump of FIG. 10 when both poppets have been manually opened.

When so desired, wall 13 is compressed causing reservoir poppet 20 to unseat itself and contact cylinder poppet 22 which, in turn, unseats that valve as well. Thus, fluid from the cylinders can be returned to the reservoir. This situation is illustrated in FIG. 13 and illustrates how the interaction of connection spring 100 and reservoir poppet 20 will facilitate this movement.

Figure 14:
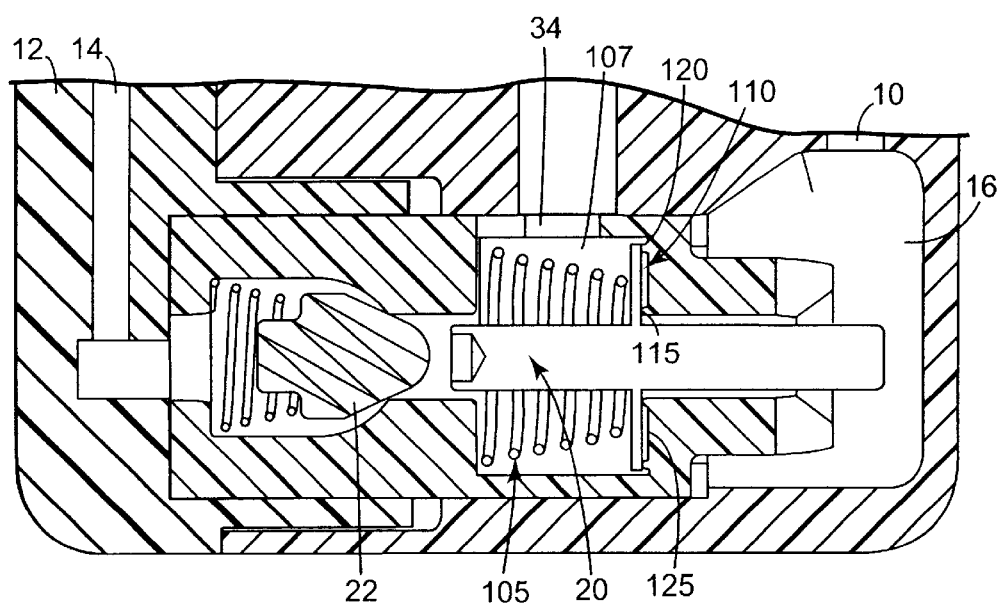
FIG. 14 is a side sectional view of a housing for a penile pump wherein the reservoir poppet includes a relatively large biasing spring and a large diameter poppet face which abuts the two-spaced lip seals.

Referring to FIG. 14, a sixth embodiment of the present invention is illustrated. A biasing spring 105, exerting a large amount of force, is coupled to reservoir poppet 20 keeping it in its closed position. Because of the large amount of force being exerted, biasing spring 105 will be able to resist high forces generated during an overpressurization situation and, thus, preventing spontaneous inflation.

Because biasing spring 105 is significantly stronger than those in the previous embodiments, it also makes it harder to open reservoir poppet 20 with the level of vacuum forces generated by the pump bulb 18. To overcome this issue, poppet face 110 is made significantly larger than in the previous embodiments. That is, the surface area of poppet face 110 has a diameter that approximates the diameter of intermediate chamber 107, which houses reservoir poppet 20. Though the amount of pressure generated by the suction of release pump bulb 18 will be fixed, by increasing the surface area of poppet face 110, the negative force generated will be greatly increased and will allow biasing spring 105 to be overcome.

As illustrated, the portion of housing 12 in contact with poppet face 110 when reservoir poppet 20 is closed, is not simply a planar configuration. As a practical matter, it is too difficult to manufacture a planar surface which will flushly and repeatedly coact with a planar poppet face 110 to consistently form a fluid-tight seal. Instead, a pair of flexible lip seals is provided. That is, inner lip seal 115 and outer lip seal 120 are provided and define a recessed portion 125 between them. Outer lip seal 120 contacts an outer portion of poppet face 110 preventing suction forces from interacting with the rear portion of poppet face 110 and holding it in place during a refilling of pump bulb 18. Inner lip seal 115 prevents fluid pressure generated during an overpressurization situation from acting against a majority of poppet face 110, which would otherwise eliminate much of the benefit of having a larger biasing spring 105. Lip seal 115 acting in conjunction with the forces generated by biasing spring 105 allows poppet face 110 to form a fluid-tight seal despite any irregularities in either poppet face 110 or housing 112. During an overpressurization situation, pressurized fluid from reservoir chamber 16 interacts with only a very small area of poppet face 110. The force generated will be insufficient to move biasing spring 105, thus, reservoir poppet 20 will remain in the sealed position preventing spontaneous inflation.

Figure 15:
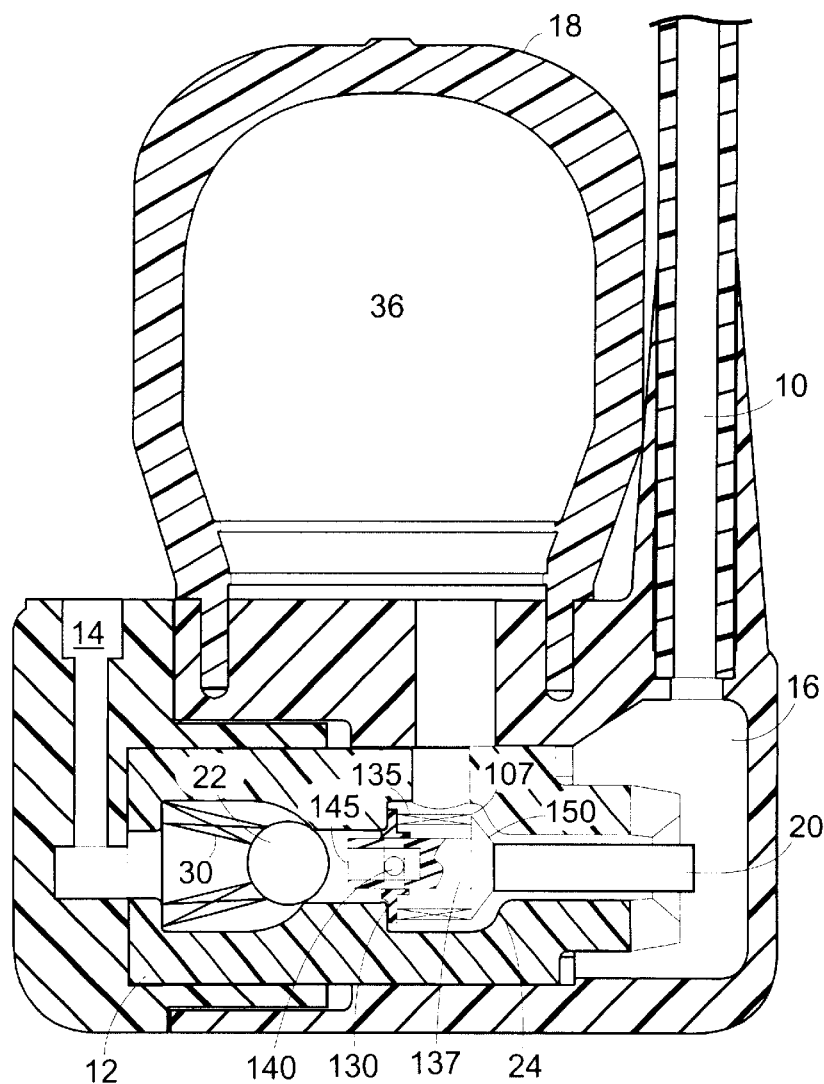
FIG. 15 is a side sectional view of a housing for a penile pump having a reservoir poppet that includes a slidable valve seal that selectively includes a throughbore leading to an outlet in the reservoir poppet.
Figure 16:
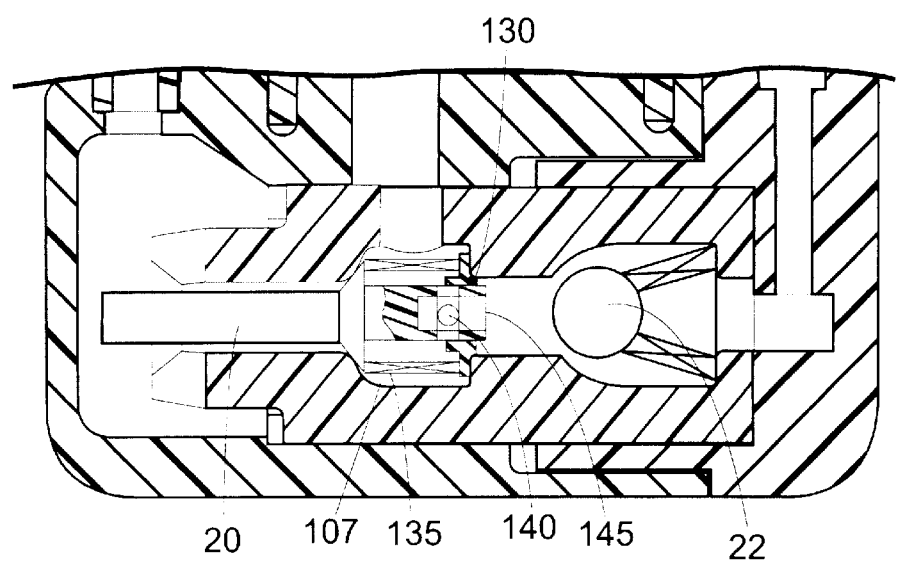
FIG. 16 is a side sectional view of the penile pump illustrated in FIG. 15 during a compression of the pump bulb.

Referring to FIG. 15, a seventh embodiment of the present invention is illustrated. Once again, a reservoir poppet 20 and cylinder poppet 22 are provided to selectively occlude a common passageway 33 between a reservoir chamber 16 and a fluid output 14. As in the previous embodiments, a front face 150 of reservoir poppet 20 abuts valve seat 24 to prevent fluid flow from reservoir chamber 16. In this embodiment this occurs in two different situations. That is during a compression of pump bulb 18 (as illustrated in FIG. 16) and during an unused situation when no overpressurization is occurring (as illustrated in FIG. 17).

Extending behind front face 150 is a rear section 137 of poppet 20. At least a portion of rear section 137 is hollow and is in fluid communication with throughbore 140 (a plurality of throughbores 140 can also be provided). Outlet 145 forms a terminus of rear section 137 and is also in fluid communication with the hollowed out portion. A valve sleeve 130 slides over rear section 137 and is held in a spaced relationship from front face 150 by slide spring 135 which biases front face 150 away from valve sleeve 130. The movement of valve sleeve 130 with respect to rear section 137 selectively seals and unseals throughbore 140.

Figure 17:
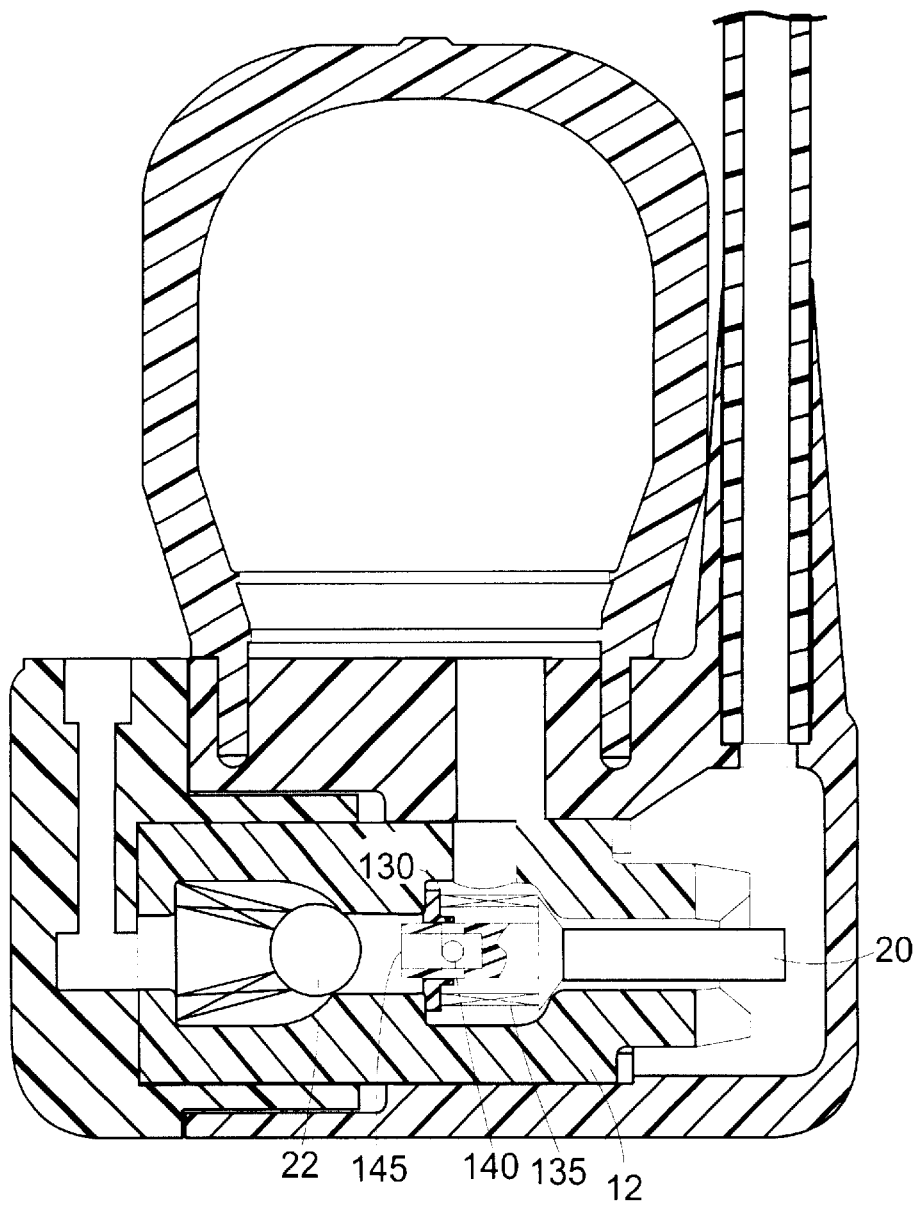
FIG. 17 is a side sectional view of the penile pump illustrated in FIG. 15 when no forces are being generated.

As illustrated in FIG. 17, under normal conditions valve sleeve 130 is abutting a portion of housing 12. Slide spring 135 biases front face 150 of poppet 20 against valve seat 24. In this situation, it is front face 150 that prevents fluid flow from reservoir 16.

During an overpressurization situation, as illustrated in FIG. 15, the forces generated within reservoir chamber 16 serve to unseat front face 150 causing it to move away from valve seat 24. To accomplish this, slide spring 135 must be at least partially compressed. In other words, overpressurization forces must be sufficient to compress slide spring 135 to cause this to occur. As front face 150 is unseated, rear section 137 moves through valve sleeve 130, since valve sleeve 130 is pressed firmly against a portion of housing 12. This action causes throughbore 140 to be occluded by valve sleeve 130. Therefore, even though pressurized fluid is able to enter into chamber 107, it is unable to pass through valve sleeve 130 and enter throughbore 140. Consequently, pressurized fluid never reaches cylinder poppet 22 and is, therefore, unable to unseat it and cause spontaneous inflation.

During compression of the pump bulb 18 (FIG. 16), pressurized fluid enters intermediate chamber 107 forcing front face 150 to firmly abut against valve seat 24. At the same time valve sleeve 130 is pressed firmly against its respective portion of housing 12. Since valve sleeve and front face 150 are spaced at their maximum distance, throughbore 140 is exposed and pressurized fluid from pump bulb 18 is able to pass through and unseat cylinder poppet 22 leading to an inflation of the cylinders.

Figure 18:
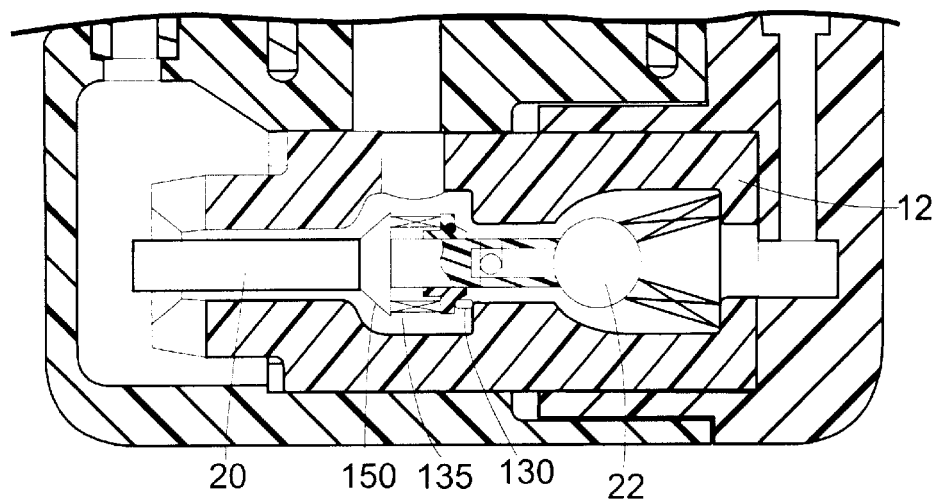
FIG. 18 is a side sectional view of the penile pump illustrated in FIG. 15 when both poppets have been manually opened.

FIG. 18 illustrates how a manual release of a reservoir poppet 20 can unseat both the reservoir poppet 20 and cylinder poppet 22 allowing for deflation of the cylinders. Sleeve 130 is forced toward front face 150 by the pressure in the cylinders once cylinder poppet 20 is unseated.

Figure 18A:
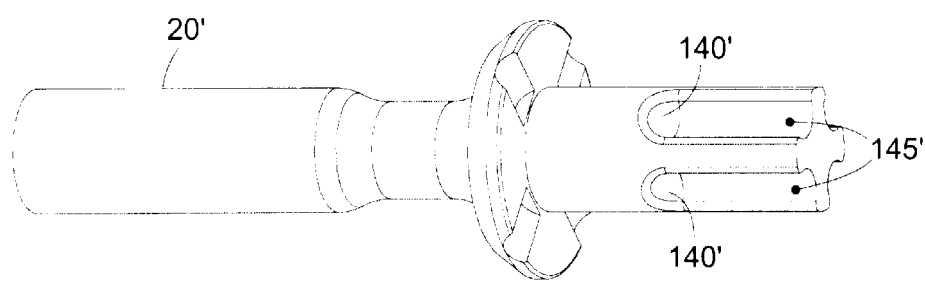
FIG. 18A is a perspective view of an alternate embodiment of a poppet usable in the penile pump in accordance with the present invention.

Referring to FIG. 18A, a poppet 20' is disclosed that can alternatively be incorporated into previous embodiments of the invention in place of poppet 20. The alternative poppet 20' includes a plurality of flutes 145' that loosely correspond in function to the output 145 discussed previously. Similarly, the lower, curved ends 140' of the flutes 145' loosely correspond in function to the throughbore 140 discussed previously.

Referring to FIGS. 19–22, an eighth embodiment of the present invention is illustrated. Housing 12 includes common passageway 33 that fluidly couples reservoir chamber 16 to fluid output 14 and is fluidly coupled to pump passageway 34. Housing 12 also includes a tapered reservoir poppet valve seat 24 configured to interact with a similarly tapered front face 210 of reservoir poppet 20. An annulus 205 is formed within housing 12 and is spaced away from, but proximate to, valve seat 24. Annulus 205 is configured to provide an opening 207 that is slightly smaller than front face 210. Annulus 205 is a semi-rigid portion of housing 12 that allows passage of front face 210 through opening 207 by moderate deflection. In other words, even though front face 210 is slightly larger than opening 207, it can still be forced therethrough. Comparing FIG. 19 with FIG. 21 also sees this relationship.

Housing 12 also includes a conical lip seal 200, which is positioned just forward of cylinder poppet 22. Conical lip seal 200 is a flexible member that interacts with a stem 215 of reservoir poppet 20. Stem 215 is generally cylindrical and includes a V-shaped groove 220 extending around its circumference. Groove 220 thus defines a medial stem section 225 that lies between groove 220 and front face 210. Medial stem section 225 is generally cylindrical.

Reservoir poppet 20 can be placed into three distinct configurations that define an activated state, a deactivated state, and a draining or open state. In the activated state (FIG. 19), pump bulb 18 can be used to inflate the cylinders. Reservoir poppet 20 is also maintained in the activated state while the cylinders are to remain inflated. In the draining state illustrated in FIG. 21, the cylinders can be emptied. Reservoir poppet 20 is placed in the deactivated state during periods of nonuse to prevent spontaneous inflation.

Figure 19:
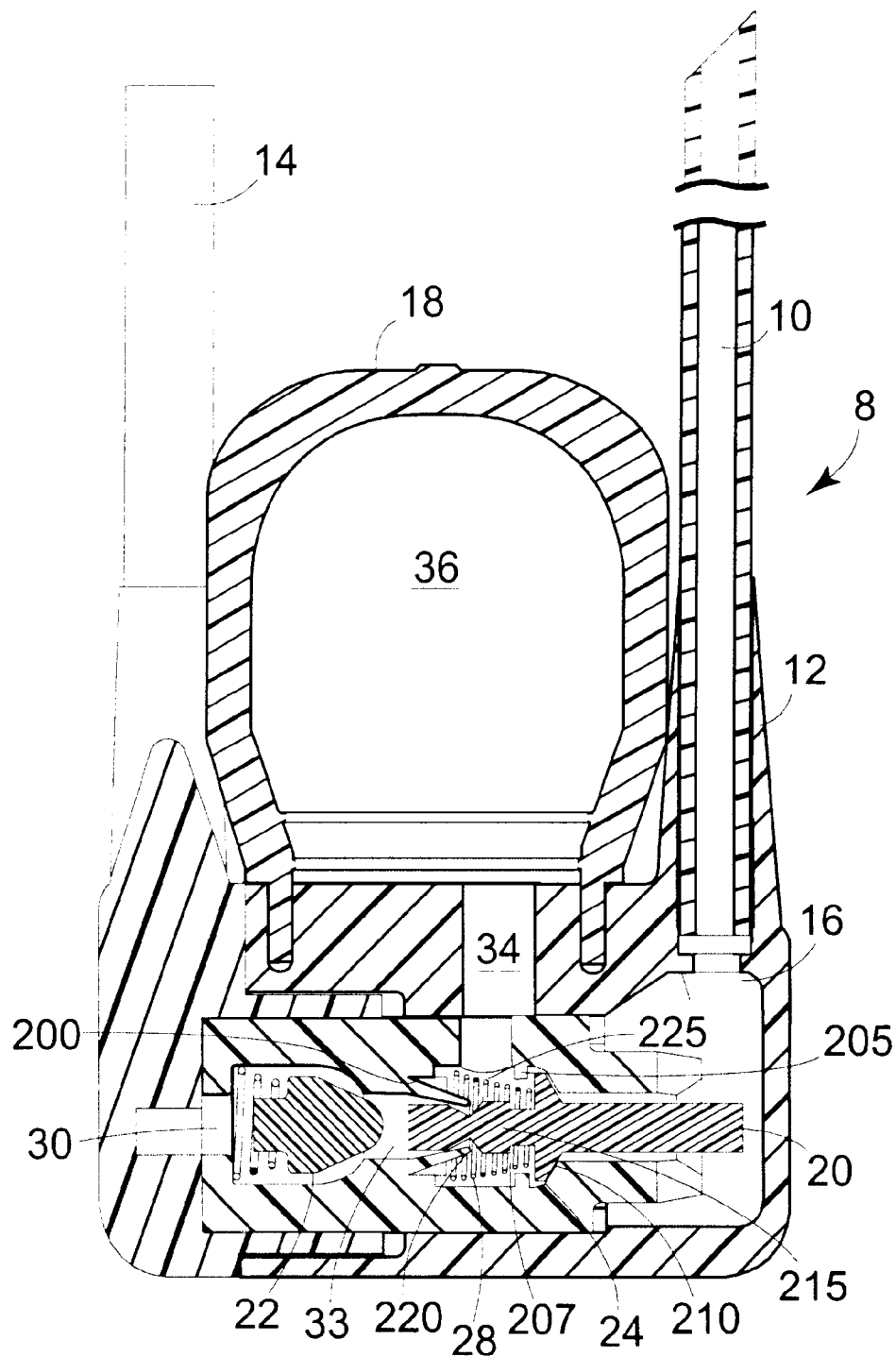
FIG. 19 is a side sectional view of a penile pump assembly including a conical lip seal and an annular ring that interact with a reservoir poppet having a grooved stem and an abutting face.

FIG. 19 illustrates pump assembly 8 in the activated state. Front face 210 is positioned between annulus 205 and valve seat 24. When so positioned, reservoir poppet spring 28 biases front face 210 against valve seat 24. If pump bulb 18 is compressed, the fluid pressure generated reinforces the biasing action of reservoir poppet 20, and causes front face 210 to further abut valve seat 24. At the same time, cylinder poppet 22 is unseated and fluid is forced into the cylinders. When reservoir poppet 20 is so positioned, V-shaped groove 220 is aligned with conical lip seal 200. This effectively prevents conical lip seal 200 from interfering with fluid flow in either direction. That is, the configuration of conical lip seal 200 is such that it cannot effectively prevent fluid flow in a direction from cylinder poppet 22 towards reservoir chamber 16. Fluid flow in the opposite direction is also unhindered (in the activated state) because groove 220 permits fluid pressure levels to increase "underneath" conical lip seal 200 (i.e., between lip seal 200 and stem 215), thus fluid flow is permitted from pump chamber 36 to the cylinders. FIG. 19 illustrates this configuration during a compression of pump bulb 18.

Figure 20:
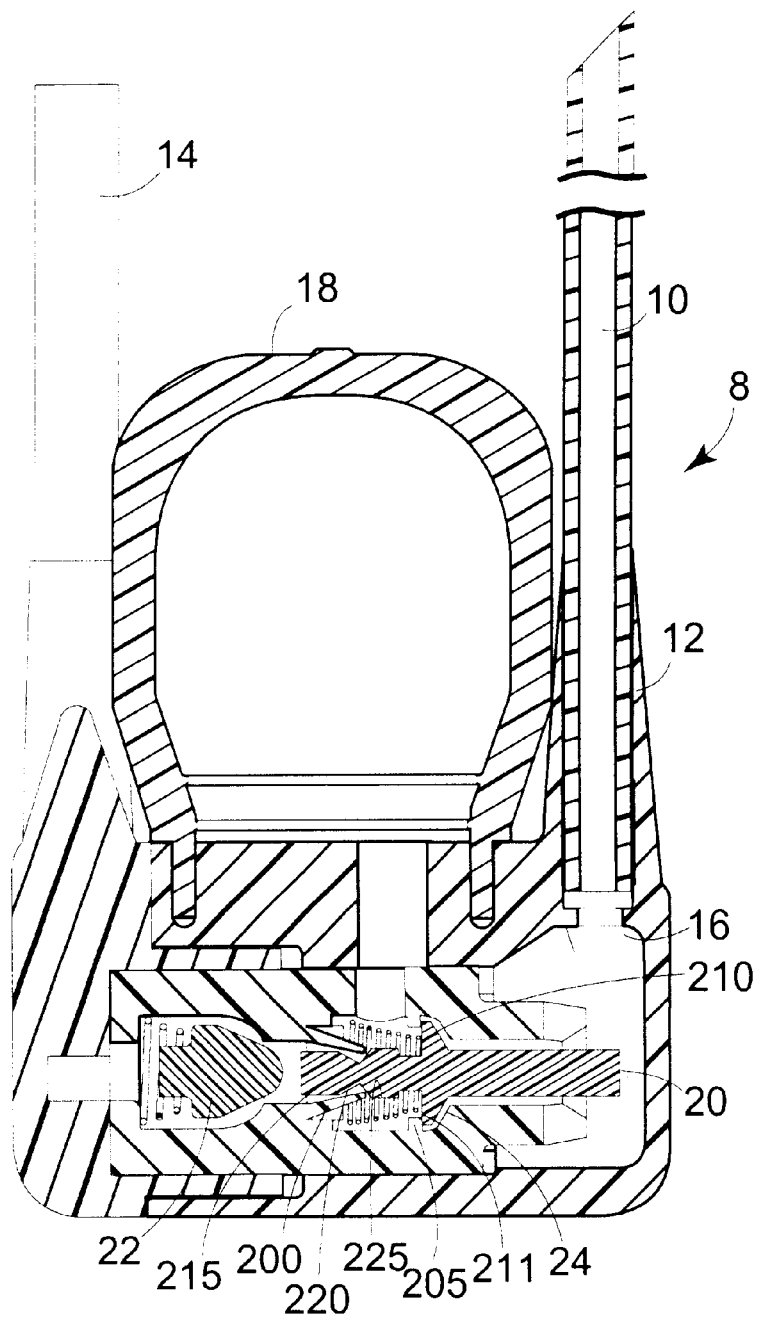
FIG. 20 is a side sectional view of the pump assembly of FIG. 19 with the cylinder poppet unseated.

FIG. 20 illustrates the configuration of the components during a release of pump bulb 18. The vacuum generated works with the biasing force of cylinder poppet spring 30 to cause cylinder poppet 22 to seal. The vacuum forces also cause front face 210 to be pulled away from valve seat 24. This allows fluid to flow from reservoir chamber 16 into pump chamber 36. While the vacuum forces are sufficient to unseat front face 210, they are insufficient to cause it to pass through annulus 205; thus, back face 211 of reservoir poppet 20 abuts annulus 205 or (depending on the spring forces involved) is held between annulus 205 and valve seat 24. In either case, fluid as able to flow into pump chamber 36. After a number of compressions of pump bulb 18, the cylinder will be inflated. While the cylinders are to remain inflated, pump assembly 8 is kept in the activated state.

During a release of pump bulb 18, the vacuum forces generated may be sufficient to cause back face 211 to seal against annulus 205. If this occurs, the pump assembly may lock up and remain in this position. That is, pump bulb 18 will be at least partially compressed and the vacuum generated will be sufficient to keep reservoir poppet 20 sealed against annulus 205, preventing fluid from moving from the reservoir to pump chamber 36. All that need be done to relieve the vacuum is manually compress the sidewall to cause reservoir poppet 20 to unseat.

Figure 20A:
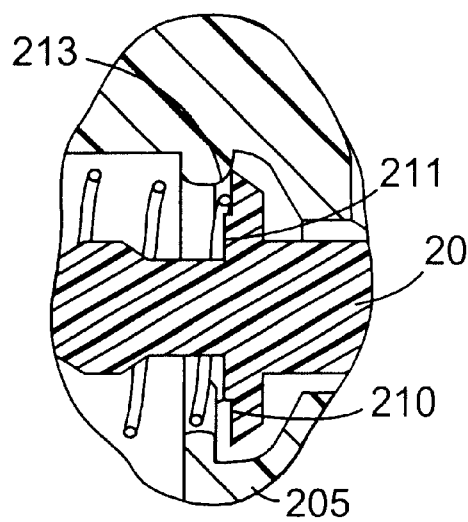
FIG. 20A is a side sectional view illustrating how the reservoir poppet may be spaced from the annulus to effect fluid flow.
Figure 20B:
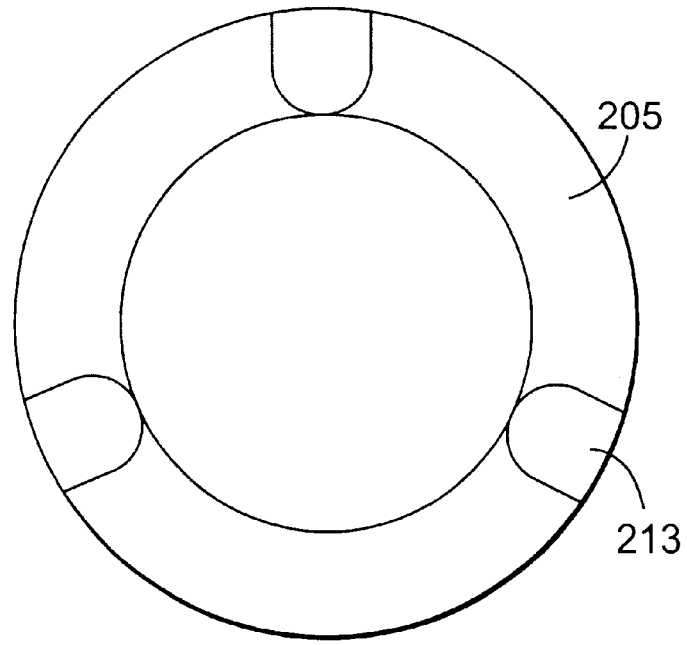
FIG. 20B is front planar view of an annulus with a plurality of spacers.
Figure 21:
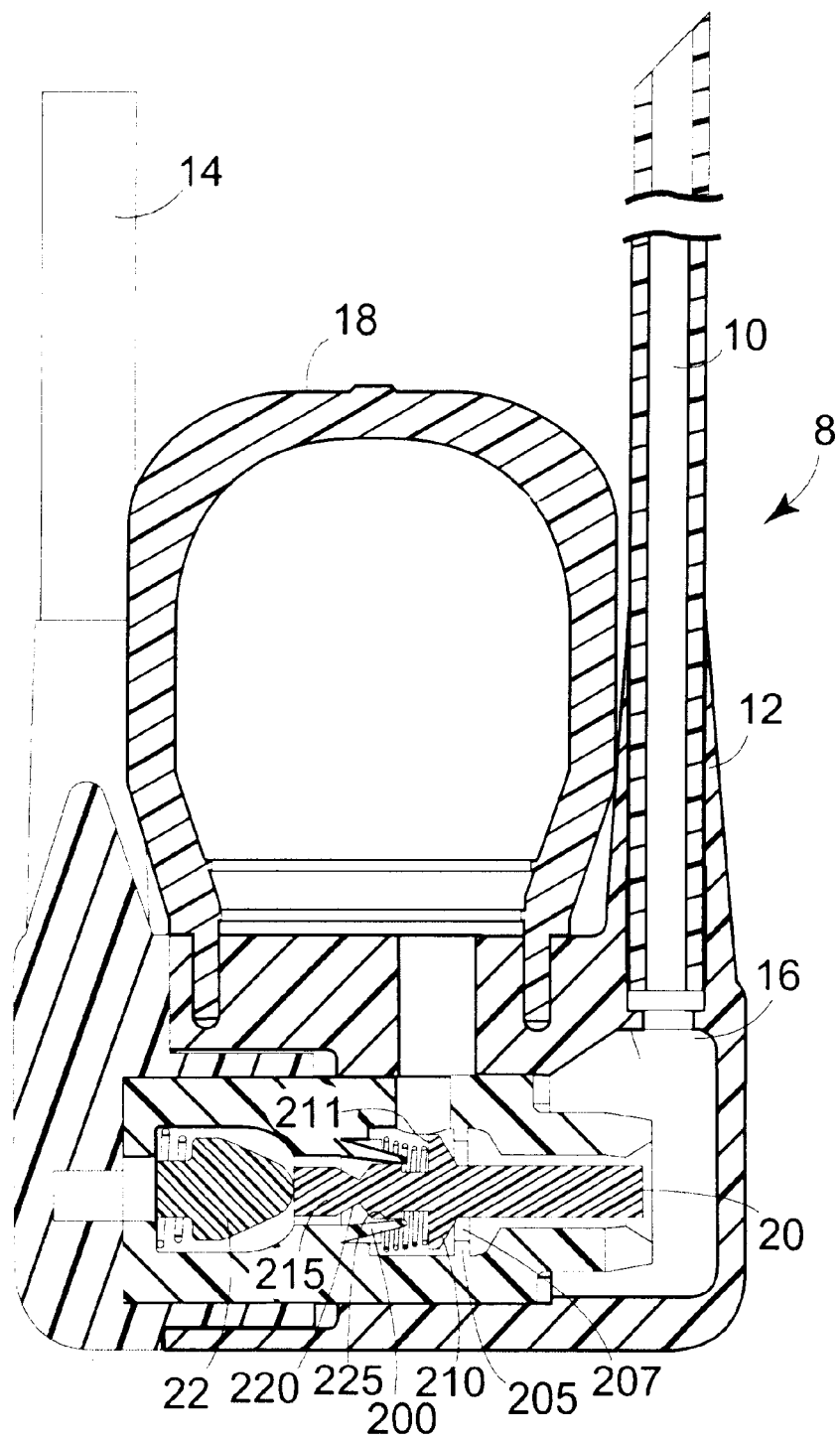
FIG. 21 is a side sectional view of the pump assembly of FIG. 19 while the cylinders are being deflated.

This situation may be confusing to patients and they may not realize the nature of the problem. Thus, a modified annulus 205 (and/or a variation in reservoir poppet 20) can be provided to prevent the situation from occurring. Referring to FIGS. 20A and 20B, such a modified annulus 205 is illustrated. Annulus 205 includes a number of spacers 213 positioned about annulus 205 and facing valve seat 24. Spacers 213 are positioned so that when rear face 211 is in contact with them, there is still a fluid path around reservoir poppet 20 and through annulus 205. That is, there is never an opportunity for rear face 211 to seal against annulus 205.

The nature and number of spacers 213 can vary. Providing three spacers allows full support of rear face 211. That is, rear face 211 is not caused to pivot by only being supported at one or two points. This pivoting action is not necessarily detrimental, and one or two spacers 213 could be utilized. More could also be utilized, so long as sufficient fluid flow is permitted. The actual size and shape of spacers 213 will depend upon the methods utilized to form them. Any size, shape and configuration is permissible so long as fluid flow sufficient to prevent the above described vacuum lock is permitted. Finally, spacers 13 could be attached to rear face 211 rather than annulus 205 to permit appropriate fluid flow.

Alternatively, various other methods could be employed to achieve the same result. So long as fluid flow around rear face 211 and through annulus 205 is permitted, this potential problem is avoided. There are solutions other than providing spacers. For example, one or more grooves could be cut into rear face 211 to achieve the same result. Various other access ports or passageways could likewise be provided. Of course, these various techniques could be combined in any number of ways.

Figure 22:
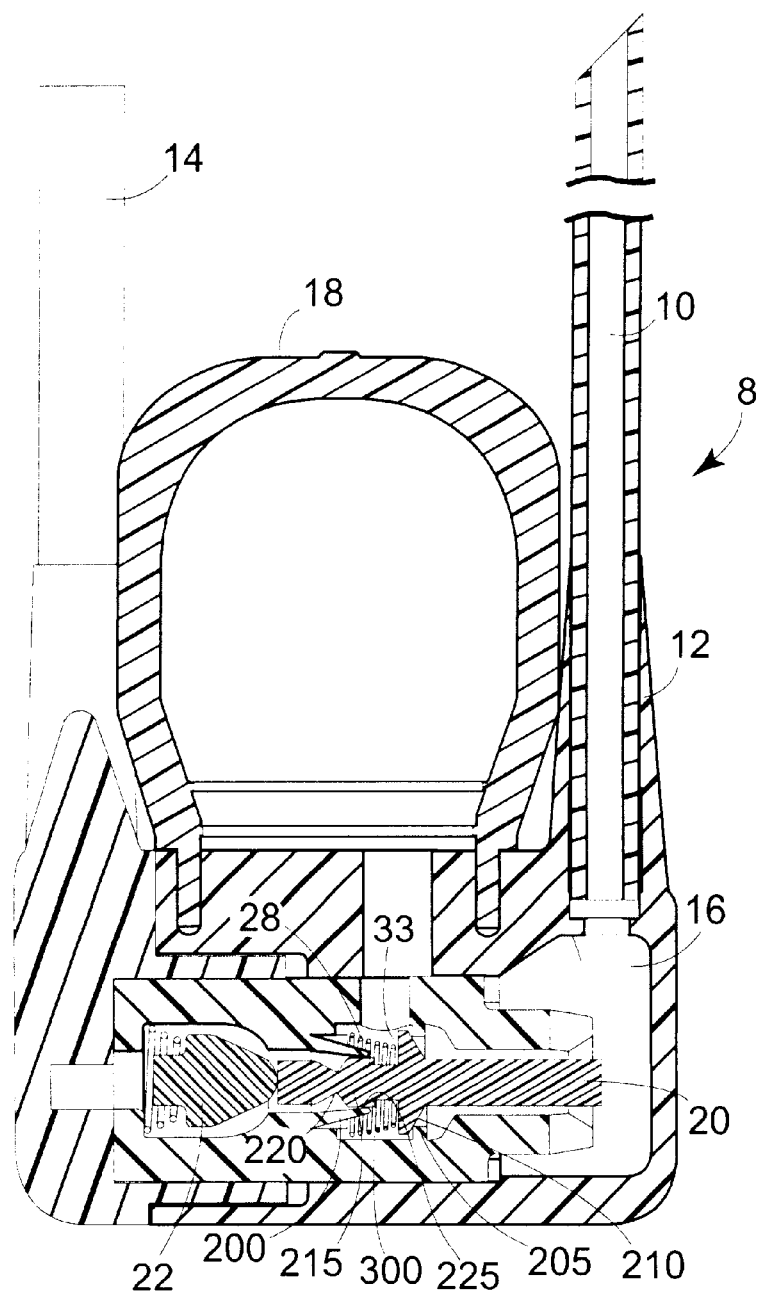
FIG. 22 is a side sectional view of the pump assembly of FIG. 19 while in a deactivated state, which serves to inhibit spontaneous inflation.

After use, when the operator wishes to deflate the cylinders, the sidewalls of housing 12 are compressed. This forces reservoir poppet 20 to move from the activated position, past the deactivated position (as shown in FIG. 22) and into the draining state, by causing front face 210 to move through annulus 205 to the position illustrated in FIG. 21. Furthermore, this movement of reservoir poppet 20 causes it to engage cylinder poppet 22 and unseat it as well as moving front face 210 away from annulus 205. Fluid is then able to flow from the cylinders into the reservoir.

When the cylinders are satisfactorily deflated, housing 12 is released. Referring to FIG. 22, reservoir poppet spring 28 biases front face 210 against annulus 205. As shown, reservoir poppet 20 is in the deactivated position. In this position, conical lip seal 200 engages medial stem section 225, which is cylindrical in nature and approximates conical lip seal 200 in size and shape. Should a compression of the reservoir cause an overpressure situation, increased fluid pressure will force reservoir poppet 20 to be moved back from annulus 205 and allow reservoir pressure to enter intermediate space 300. Without lip seal 200, reservoir pressure would enter common passageway 33 and open cylinder poppet 22 causing spontaneous inflation. However, reservoir pressure will act on conical lip seal 200 causing it to firmly seal against medial stem section 225, thus preventing fluid pressure from acting on cylinder poppet 22 and thus preventing spontaneous inflation.

The operator must place pump assembly 8 in the deactivated state during periods of non-use to effectively prevent spontaneous inflation. When the operator desires to inflate the cylinders and pump assembly 8 is in the deactivated state, all that is required is a compression of pump bulb 18. As pump bulb 18 is compressed, fluid pressure levels within intermediate space 300 are rapidly increased to relatively high levels. Conical lip seal 200 continues to prevent fluid flow therethrough (thus preventing an unseating of cylinder poppet 22); however, the higher pressures being generated are sufficient to force front face 210 through annulus 205. Thus a compression of pump bulb 18 causes reservoir poppet 20 to move from the deactivated position to the activated position, from which the cylinders are inflated in the above described manner.

FIGS. 23–28 illustrate alternative embodiments of a reservoir poppet 318 and a pump and valve assembly 300 in which certain modifications have been made to improve performance. The functionality and operability of the arrangement of FIGS. 23–28 is discussed in co-pending application Ser. No. 09/749,075 entitled "Penile Pump With Side Release Mechanism" which was filed on Dec. 27, 2000, and Ser. No. 09/749,075 Dec. 27, 2000 entitled "Improved Penile Pump With Side Release Mechanism," filed concurrently herewith, the entire disclosure of which is herein incorporated by reference.

Figure 23B:
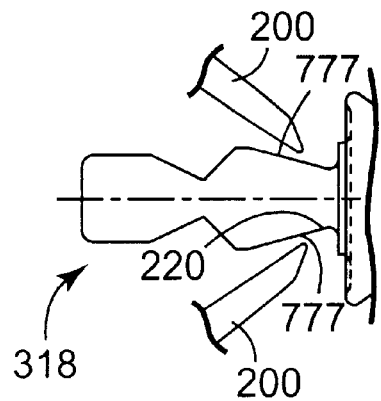
FIGS. 23B and 23C are more detailed illustrations of portions of the reservoir poppet, with FIG. 23B showing a poppet taper and FIG. 23C showing an alternative design.
Figure 23A:
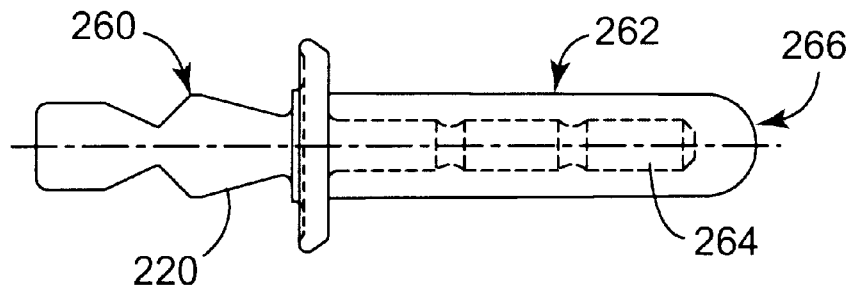
FIG. 23A shows a side view of an alternative embodiment of the entire reservoir poppet including a plastic portion.
Figure 24:
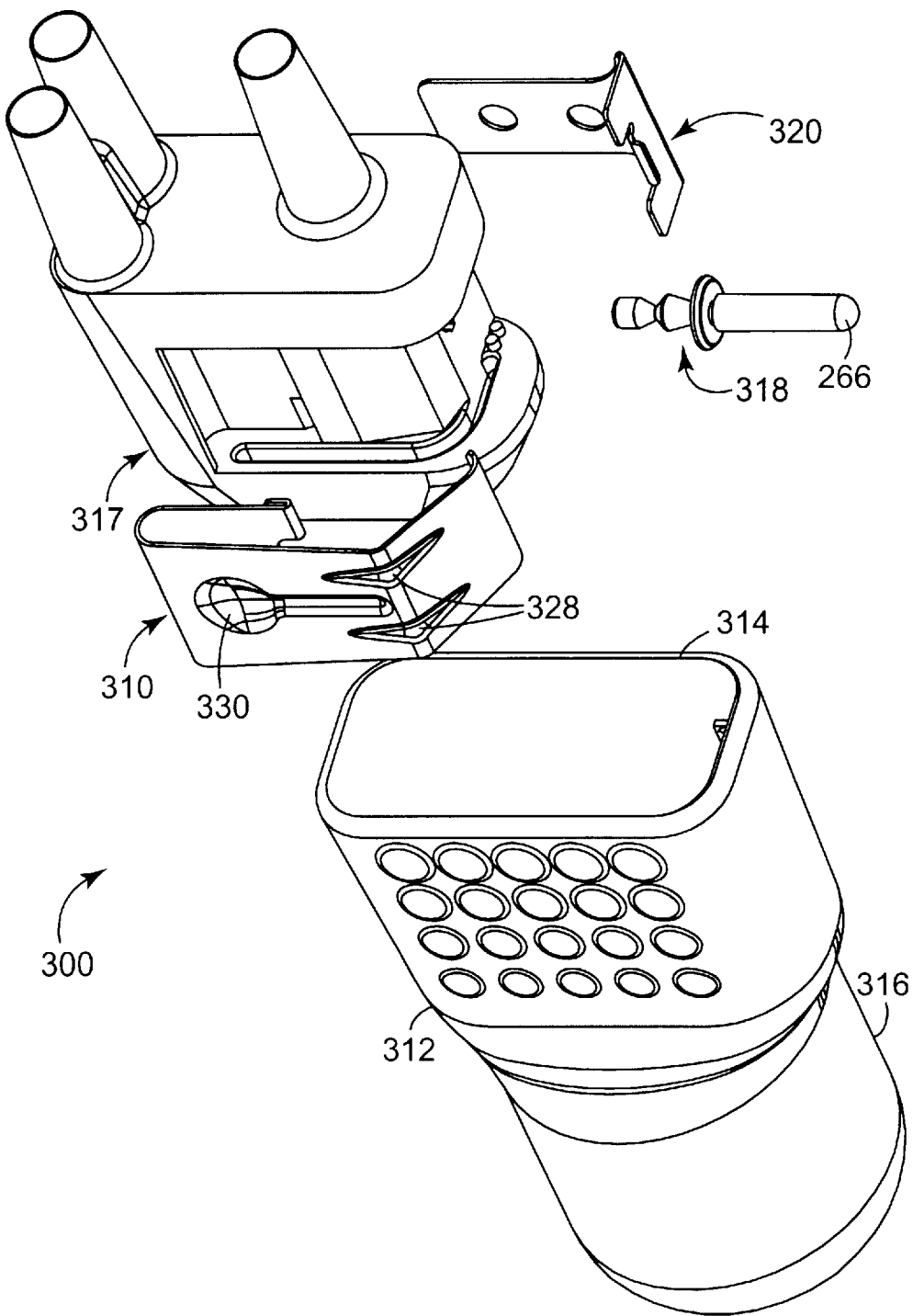
FIG. 24 is an exploded perspective view of an alternative embodiment of the present invention.

As shown in FIG. 23A, a reservoir poppet 318 comprises an elongate rigid member 260 and a synthetic member 262. Synthetic member 262 is disposed over a segment/post portion 264 of the rigid member 260. Rigid member 260 is preferably made of a metal material, such as steel, stainless steel, or the like. Synthetic member 262 is preferably made of a strong, durable plastic material, for example, acetal, nylon and/or polyester, to prevent undesired frictional contact with another metal member, such as an actuating bar described below. Synthetic member 262 is rigidly attached to rigid member 260 by molding, bonding, or the like. Synthetic member 262 prevents premature wearing of reservoir poppet 318 and another member. For example, synthetic member 262 may prevent direct metal-on-metal contact of metal reservoir poppet 318 with an actuation bar 310, as shown in FIG. 24. The addition of synthetic member 262 reduces the frictional interaction of reservoir poppet 318 and another metal member, which typically occurs at an end 266 of reservoir poppet 318. Thus, the risk of marking or deforming reservoir poppet 318 and the engaging metal member is reduced, and the useful life of the two components is extended.

Figure 23C:
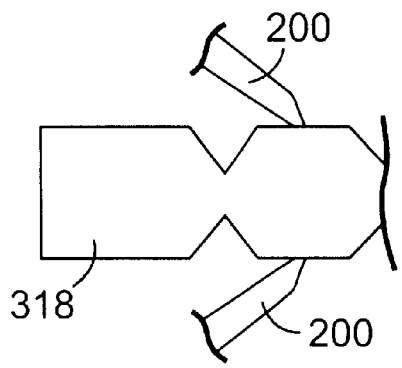

As disclosed in the embodiments of FIGS. 19–22 above, V-shaped groove 220 is sized and shaped to operably associate with lip seal 200 to prevent lip seal 200 from interfering with fluid flow at predetermined relationships between the poppet 318 and lip seal 220. As shown in the embodiment of FIG. 23B, poppet 318 has a poppet taper 777. In operation, when poppet 318 is pushed back into the release or deflation mode (see FIG. 26C), taper 777 permits lip seal 200 to separate from poppet 318. This allows fluid from the cylinder to pass unimpeded through the pump. Without taper 777, lip seal 200 would rest on reservoir poppet 318 as shown in FIG. 23C. The arrangement of FIG. 23C requires pressure to open lip seal 200 before fluid is allowed to pass from the cylinder to the reservoir. Moreover, when the pressure drops below a minimum value, lip seal 200 closes on poppet 318 and traps pressurized fluid in the cylinder. This typically happens at a less than flaccid cylinder condition. Unfortunately, to force this pressurized fluid out of the cylinder when it is at this state, the patient must squeeze his penis and the cylinder to increase cylinder pressure and open the lip seal design. For these reasons, the embodiment shown in FIG. 23C is a less preferred design.

As discussed in the embodiments above, in some patients it may be difficult to achieve compression because of the relatively small size of pump bulb 18. Likewise, it may be difficult for certain patients to grasp valve housing 12 in the proper manner since valve housing 12 may slip out of position between the patient's fingers. Thus, an alternative pump and valve assembly 300 is provided as shown in FIGS. 24–28.

FIG. 24 shows an exploded view of the alternative pump and valve assembly 300 with an actuating bar 310, a pump bulb 316, a reservoir poppet 318, and a poppet support 320. Assembly 300 comprises a valve block 317 for housing the fluid passageways that inter-connect inflatable cylinders and a reservoir (not shown), as discussed in the embodiments above. Actuating bar 310, having a plurality of ribs 328 and 330, attaches to a side of valve block 317 and is positioned to engage an end of a reservoir poppet 318. Reservoir poppet 318 is a check valve that operates to control fluid flow into and out of a reservoir, and is to be positioned within fluid passageways of valve block 317. Poppet support 320 is to be disposed on an end of valve block 317, proximate an end 266 of reservoir poppet 318, to prevent sideways sliding of reservoir poppet 318 during actuation of the pump. Pump bulb 316 is to be located over the valve block 317, actuating bar 310, reservoir poppet 318, and poppet support 320. Pump bulb 316 comprises major panels 312 and 314 with textured surfaces that allow patients to easily identify that portion of the valve assembly 300. When a patient applies pressure to major panels 312 and 314 of pump bulb 316, major panel 312 engages actuating bar 310. This allows the patient to grasp the major panels 312 and 314 to cause actuating bar 310 to force reservoir poppet 318 to move to an open position, permitting the flow of fluid through the channels of valve block 317. Actuating bar 310 and poppet support 320 are described in detail below.

Preferably, reservoir poppet 318 of the embodiment of FIG. 24 is substantially the same as hybrid metal and synthetic reservoir poppet 318 disclosed in FIG. 23A and discussed above.

Figure 25:
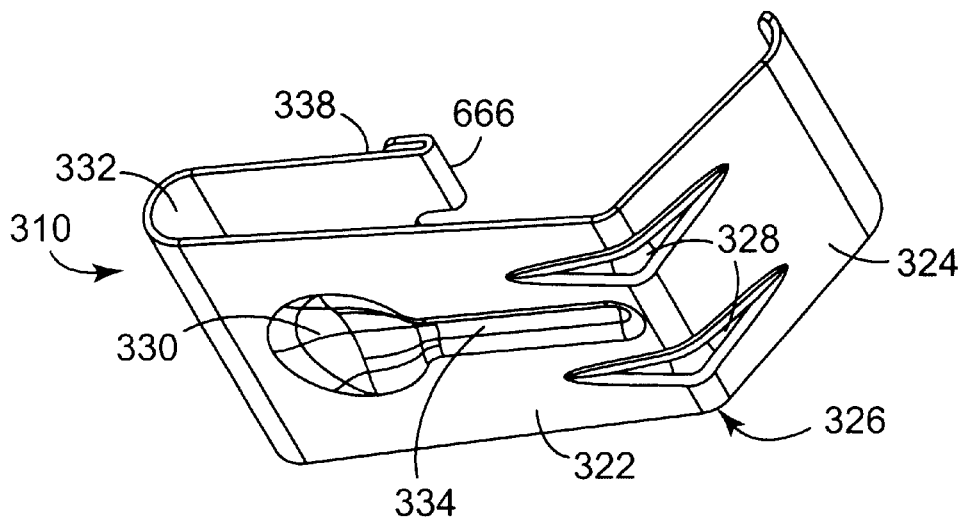
FIG. 25 is perspective view of the actuating bar of the embodiment of FIG. 24.
Figure 26A:
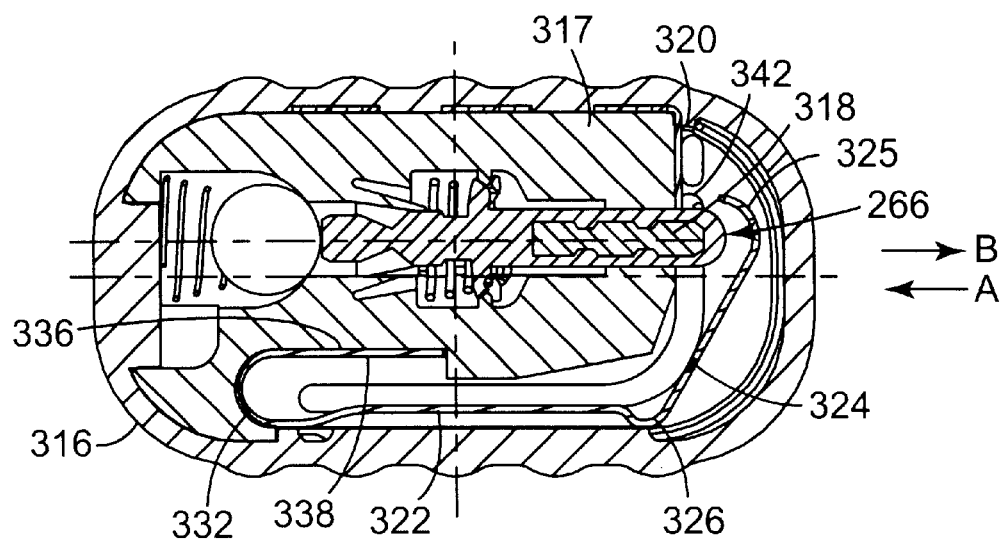
FIG. 26A is a top sectional view of the embodiment of FIG. 24.
Figure 26B:
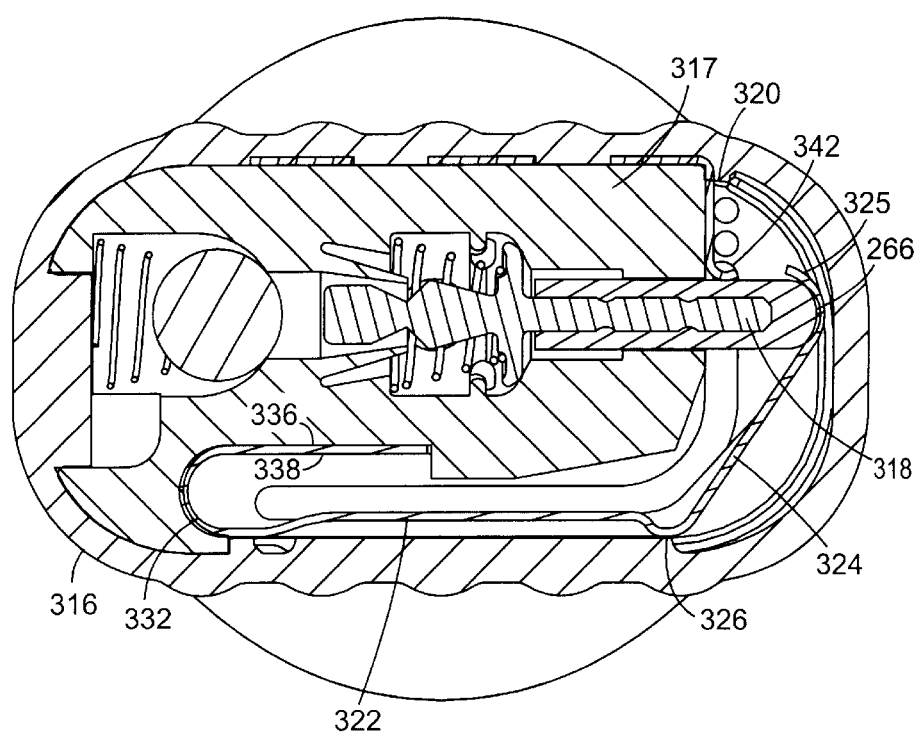
FIG. 26B is a top sectional view of the embodiment of FIG. 24 showing the elements in a position when both cylinders are inflated.

As illustrated in FIGS. 24–26, actuating bar 310 is a thin elongated member formed to comprise an actuating face 322 and an actuating arm 324 that are connected by an angle portion 326. A U-shaped portion 332 connects a connecting end 338 to actuating face 322.

Connecting end 338 includes two forked portions 666, one of which is shown in FIG. 25. As shown in FIG. 26A, actuating bar 310 is disposed within valve block 317 by securement of end 338 into a valve block interface 336. The forked portions 666 of connecting end 338 help hold actuating bar 310 in place.

Angle portion 326 provides actuating bar 310 with a spring force that is applied to an end 266 of reservoir poppet 318. Angle portion 326 permits actuating face 322 of actuating bar 310 to extend along the length of valve block 317 while actuating arm 324 extends along a side of the width of the valve block 317. The configuration of actuating bar 310 enables it to engage an end 266, e.g., the tip, of reservoir poppet 318. Actuating arm 324 includes a curved portion 325 for complementary engagement with reservoir poppet end 266. Preferably, curved portion 325 presents a smooth face to the side of the pump shell when the pump shell acts on the curved portion 325 of the actuating bar 310.

Figure 26C:
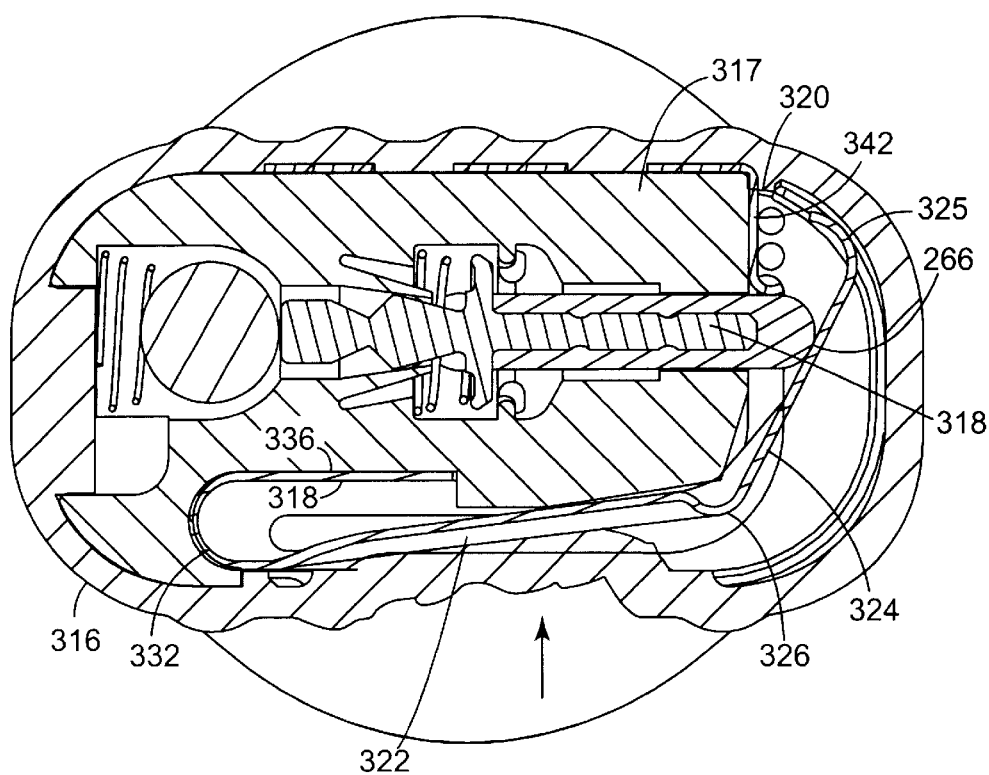
FIG. 26C is a top sectional view of the embodiment of FIG. 24 showing both valves open.

As discussed above, when the patient grasps the valve assembly in virtually any orientation and applies pressure (e.g. see FIG. 26C), actuating bar 310 acts to open the appropriate check valves. Thus, when the patient grasps a portion of the pump and valve assembly 300 other than the pump bulb 316, compression will result in the flexing of actuating bar 310. During compression, actuating face 322 flexes inwardly and actuating arm 324 flexes toward poppet end 266, as indicated by arrow A in FIG. 26A. Actuating arm 324 moves into engagement with poppet end 266. The movement of actuating arm 324 forces axial movement of reservoir poppet 318 in the same direction as arrow A and into an open position. The axial movement of the reservoir poppet 318 permits fluid to flow through the fluid pathways to the reservoir and allows the cylinders to deflate (FIG. 26C).

When the patient ceases compression of pump and valve assembly 300, actuating face 322 returns to its original position. Actuating arm 324 moves in a direction indicated by arrow B, and out of engagement with poppet end 266. This motion permits reservoir poppet 318 to move into the deactivated position, as shown in FIG. 26A.

Angle portion 326 in actuating bar 310, and its resistance to flexing outwardly, creates a desirable spring force member. This spring is the mechanism that forces reservoir poppet 318 into a position that permits the flow of fluid through the fluid pathways and back into the reservoir. For example, during patient compression of pump and valve assembly 300 (FIG. 26C), actuating arm 324 enters engagement with poppet end 266. Actuating arm 324 applies the spring force to the poppet end 266 to force reservoir poppet 318 into the interior of valve block 317 into an open position. When actuating arm 324 is engaged with poppet end 266, there is an opposing force created by the resistance of reservoir poppet 318 to movement toward the open position. This opposing force may overcome the spring force and cause actuating arm 324 to improperly deflect. Stated alternatively, this improper deflection occurs when the opposing force exerted against the spring force of actuating bar 310 overcomes the inherent spring force and causes the actuating arm 324 to bend backwards or buckle.

To prevent improper deflection, ribs 328 are formed on actuating bar 310, as shown by FIG. 25. Each rib 328 is a recess or impression formed in actuating bar 310 and extends across angle 326. Ribs 328 increase the strength and stiffness of angle portion 326, which increases the resistance to deflection during actuation. The surface area of angle portion 326 is disposed along a given plane. Ribs 328 divide the surface area of angle portion 326 with recesses that extend into another plane. The portions of material extending in a different plane increase the spring force of angle portion 326. This increase in spring force decreases the likelihood of improper deflection of actuating arm 324. The absence of improper deflection thus ensures full axial travel of reservoir poppet 318 and attainment of the open position. Additionally, reinforcement of angle portion 326 prevents any permanent deformation that might occur due to repeated actuation. This resistance to deflection or bending helps prevent fatigue of actuating bar 310 and extends the useful life of the component. Although ribs 328 may be formed by a curved recess that extends in a plane perpendicular to the surface of angle portion 326 as shown in the Figures, ribs 328 may exist in many different orientations. A sufficient number of ribs 328 may be provided to angle 326 so as to achieve a predetermined deflection resistance. For example, two ribs 328 are provided in the angle 326, as shown in FIG. 25.

When a patient compresses valve assembly 300 to deflate the prosthesis, actuating face 322 flexes or pivots inwardly about U-shaped portion 332. This causes actuating face 324 to move into engagement with poppet end 266. The repeated application of force to a particular area of actuating face 322, may cause permanent deformation. As shown in FIG. 25, a recess formed in and disposed along actuating face 322 defines a rib 330. Rib 330 strengthens and stiffens actuating face 322 to limit deformation. Rib 330 extends into a plane other than the plane created by the surface of actuating face 322 to increase its resistance to bending. During patient compression, rib 330 distributes the force applied throughout actuating face 322 rather than permit the compression force to be concentrated in one area. Thus, actuating face 322 properly flexes while resisting permanent deformation. Rib 330 may be shaped to distribute the compression force in any desired pattern. For example, as shown in FIG. 25, rib 330 may be a spoon-shaped impression centrally formed on actuating face 322 with a larger oval portion disposed toward U-portion 332 of actuating bar 310. An elongate portion 334 of spoon-shaped rib 330 extends toward angle portion 326. This shape is preferred since rib 330 helps to lower stresses and reduce deflection caused by compression forces applied to flex actuating face 322.

The relatively thin composition of actuation bar 310 is beneficial for several reasons. During actuation, U-portion 332 bends to flex actuating face 322 inwardly and actuating face 322 moves actuating arm 324 into engagement with reservoir poppet 318. After actuation, U-portion 332, actuating face 322 and actuating arm 324 return to their original position. With an actuating bar made of a thick material, U-portion 332 does not properly bend during actuation. In operation, when using a thicker actuating bar 310 U-portion 332 does not bend, and connecting end 338 is pushed into valve block 317 causing its inner cavities to distort. In turn, this causes annular ring 500 (FIG. 26) of valve block 317 to come out-of-round and impedes or stops the movement of poppet 318 in direction A. Preferably, actuating bar 310 is a thin member made of a material with a sufficient thickness and stiffness to provide the desired spring force and avoid improper deflection. For example, actuation bar 310 may be formed from a stainless steel sheet having a thickness of approximately 0.010 inches. Actuation bar 310 may be made of various metal materials, plastic, or the like.

As shown in FIG. 26C, the engagement of actuating arm 324 and poppet end 266 can be applied from one side of reservoir poppet 318. Thus, the spring force applied by actuating bar 310 is not completely along a longitudinal axis of reservoir poppet 318. The spring force is applied in both the axial and transverse/sideways directions to poppet end 266. The sideways force has the unintended consequence of tipping reservoir poppet 318 sideways into valve block 317. In response, valve block 317 tends to deform and potentially causes reservoir poppet 318 to be misaligned. This misalignment results in reservoir poppet 318 being restrained from moving axially into valve block 317 to reach an activated/open position. As shown in FIGS. 26A–28, a stiff poppet support 320 is provided to prevent the misalignment of reservoir poppet 318.

Figure 27:
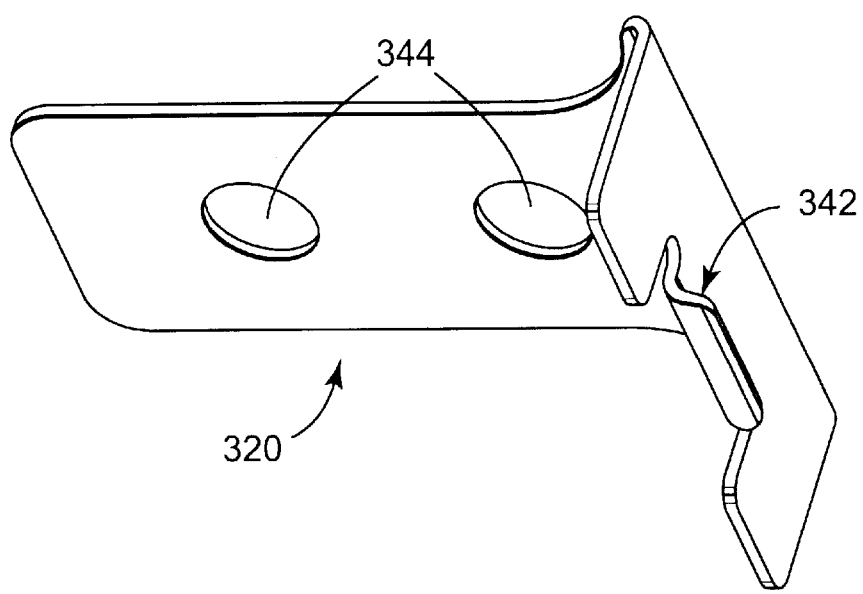
FIG. 27 is a perspective view of the poppet support of the embodiment of FIG. 24.
Figure 28:
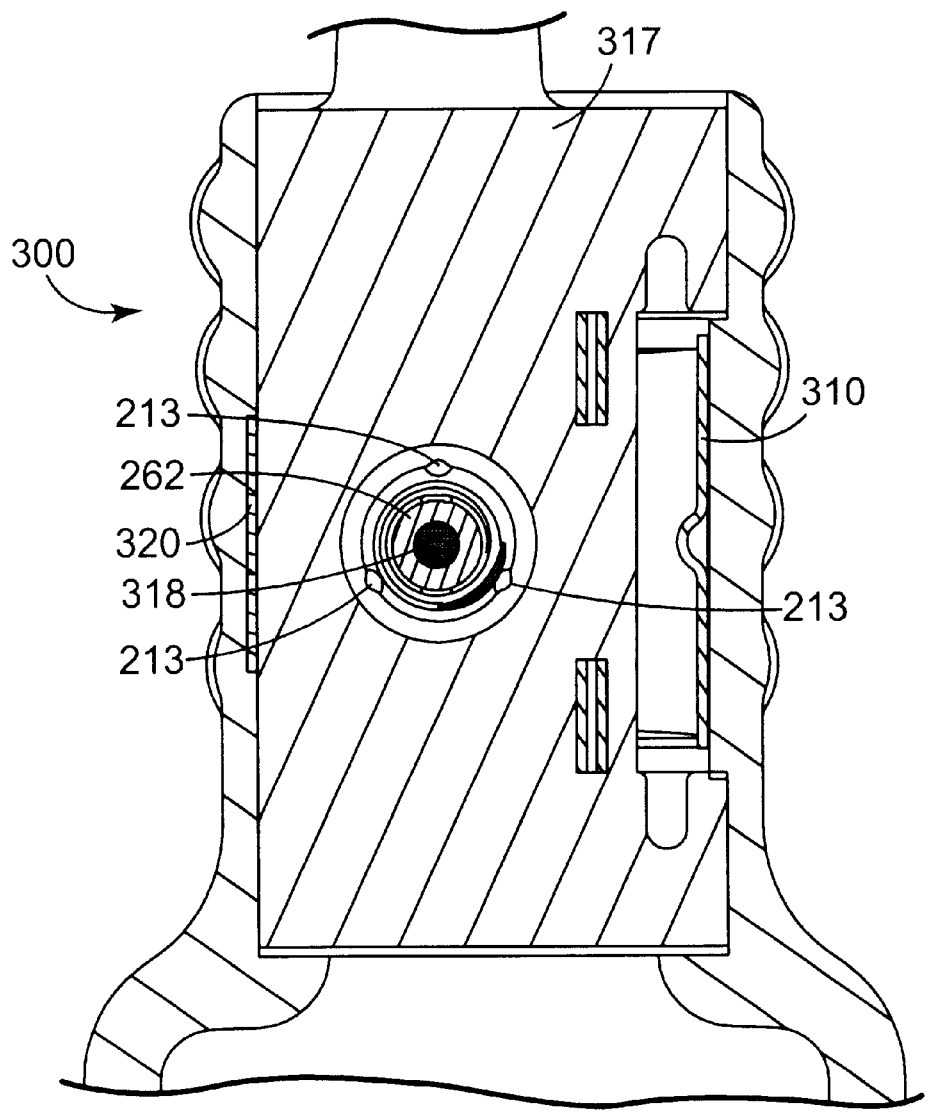
FIG. 28 is a sectional view of the embodiment of FIG. 24.

As shown in FIG. 27, poppet support 320 is an elongate, generally L-shaped member comprising a shelf 342 at one end of poppet support 320. Apertures 344 are provided in a portion of support 320 to attach the support 320 to valve block 317. See FIGS. 26 and 27. The poppet support 320 wraps around a portion of the valve block 317 and rests against a portion of poppet end 266. The shelf 342 provides a smooth surface for a segment of reservoir poppet 318 to slide axially along during reservoir poppet 318 travel between open and closed positions. During actuation, curved portion 325 of actuating bar 310 applies a spring force, comprising both axial and side forces, to move reservoir poppet 318 to an open position. Poppet support 342 prevents sideways movement of the reservoir poppet 318 as it is forced into the interior of the valve body 317. Poppet support 320 ensures the proper alignment of reservoir poppet 318 to easily move axially into valve body 317 to the open position.

Various embodiments have been shown and described to prevent spontaneous inflation. It is to be understood that though these embodiments have been shown and described in isolation, various features of each embodiment can be combined with the others to produce a variety of embodiments.

While the present invention has been described with respect to a pump and valve assembly for a penile implant, the use of generated overpressure to seal a fluid aperture has many other applications within the scope and spirit of the present invention. For example, artificial sphincters utilize fluid pressure to maintain a body cavity or natural passageway in a closed or sealed state. When actuated, fluid pressure is released from the sphincter, causing the bodies' passageway to open. As such, the fluid pressure generated could be used to assist the artificial sphincter in either state. Likewise, many other uses for an overpressure seal exist, both specifically within the field of medical devices and within the field of fluid/gas handling devices in general.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited in the particular embodiments which have been described in detail therein. Rather, reference should be made to the appended claims as indicative of the scope and content of the present invention.

What is claimed is:

1. A penile prosthesis comprising:

a housing;

a fluid inlet to the housing, the fluid inlet being adapted to couple to a reservoir;

a fluid outlet from the housing, the fluid outlet being adapted to couple to an inflatable cylinder;

a fluid passageway coupling the inlet to the outlet;

a first check valve disposed within the fluid passageway and biased towards a closed position;

a second check valve disposed within the fluid passageway and biased towards a closed position;

a pump bulb in fluid communication with the fluid passageway between the first and second check valves; and a reservoir chamber coupling the inlet to the fluid passageway, wherein a portion of the first check valve extends into the reservoir chamber and is coupled to an outer wall of the reservoir chamber so that as fluid pressure within the reservoir chamber increases, an expansion of the reservoir chamber occurs which urges the first check valve towards a closed position.

2. The prosthesis of claim 1 wherein a negative pressure generated by an expansion of the pump bulb is sufficient to open the first check valve.

3. The prosthesis of claim 1 further including a spring coupling the first check valve to the outer wall.

4. The prosthesis of claim 1 wherein the spring biases the first check valve toward the closed position so that as the fluid pressure increases in the reservoir chamber, the biasing of the spring will aid in resisting the unintentional unseating of the first check valve.

5. A penile prosthesis comprising:

a housing;

a fluid inlet to the housing, the fluid inlet being adapted to couple to a reservoir;

a fluid outlet from the housing, the fluid inlet being adapted to couple to an inflatable cylinder;

a reservoir chamber disposed within the housing and fluidly coupled to the inlet;

a fluid passageway fluidly coupled to the reservoir chamber;

a first check valve disposed within the fluid passageway and biased towards a closed position;

a second check valve disposed within the fluid passageway and biased towards a closed position;

a pump bulb in fluid communication with the fluid passageway between the first and second check valves;

a spring biasing the first check valve into the sealed position, wherein the biasing force of the spring is selected to be strong enough to oppose pressures generated in an overpressurization situation and keep the first check valve in the sealed position; and a face coupled to the first check valve wherein the face has a large diameter compared to a diameter of the remainder of the first check valve so that suction forces generated after a compression of a pump bulb act on a sufficient surface area of the face to overcome the biasing force of the spring.

6. The pump assembly of claim 5 further including: a first lip seal located within the housing for selectively engaging an inner diameter portion of the face in a substantially fluid tight manner; and a second lip seal located within the housing for selectively engaging an outer diameter portion of the face in a substantially fluid tight manner.

7. A penile prosthesis comprising: a housing;

a fluid inlet to the housing, the fluid inlet being adapted to be coupled to a reservoir;

a fluid outlet from the housing, the fluid outlet being adapted to be coupled to an inflatable cylinder;

a reservoir chamber disposed within the housing and fluidly coupled to the inlet; a fluid passageway fluidly coupled to the reservoir chamber;

a first check valve disposed within the fluid passageway and biased towards a closed position;

a second check valve disposed within the fluid passageway and biased towards a closed position;

a pump bulb in fluid communication with the fluid passageway between the first and second check valves;

a front face on the first check valve for selectively sealing and unsealing an opening to the fluid inlet;

a rear section protruding from the first check valve away from the opening, including an internal fluid passageway and a throughbore providing access into the internal fluid passageway and an outlet providing an egress from the internal fluid passageway; and a valve sleeve slidably engaging the rear section to selectively seal and unseal the throughbore so that as higher pressure levels are generated within the inlet, front face of the first check valve is caused to unseal the opening and the valve sleeve is caused to seal the throughbore, wherein the valve sleeve contacts a portion of the housing and prevents fluid flow to the outlet.

8. A penile prosthesis comprising:

a housing;

a fluid inlet to the housing, the fluid inlet being adapted to couple to a reservoir;

a fluid outlet from the housing, the fluid outlet being adapted to couple to an inflatable cylinder;

a reservoir chamber disposed within the housing and fluidly coupled to the inlet;

a fluid passageway fluidly coupled to the reservoir chamber;

a second check valve disposed within the fluid passageway and biased towards a closed position;

a first check valve disposed within the fluid passageway and biased towards a closed position, the first check valve having a front face for selectively sealing and unsealing an opening to the fluid inlet and a rear stem section protruding from the first check valve away from the opening, including a cylindrical portion and a groove;

a pump bulb in fluid communication with the fluid passageway between the first and second check valves;

a conical lip seal integral with the housing and positioned so that the rear stem section is moveable therein so that when a cylindrical portion of the stem section is aligned with the conical lip seal, fluid flow in a direction from the inlet to the outlet is prevented and increased pressure levels within the inlet serves to further seal the conical lip seal against the cylindrical portion of the stem section, and when the groove is aligned with the conical lip seal, fluid flow is permitted; and an annulus integral with the housing positioned so as to cooperate with the front face, allowing the front face to be forcibly move therethrough so that when the front face is on a first side of the annulus, the groove of the stem section is aligned with the conical lip seal and when the front face is on a second side of the annulus the cylindrical portion of the stem is aligned with the conical lip seal.

9. The penile prosthesis of claim 8, further comprising: a spacer separating a rear portion of the front face from the annulus when said front face is on said first side so that fluid flow is permitted around the rear portion and through the annulus.

10. The penile prosthesis of claim 9 wherein the spacer is a plurality of bumps located on the annulus.

11. A penile prosthesis comprising:

a housing;

a fluid inlet to the housing, the fluid inlet being adapted to couple to a reservoir;

a fluid outlet from the housing, the fluid outlet being adapted to couple to an inflatable cylinder;

a fluid passageway coupling the inlet to the outlet, the fluid passageway having a major axis;

a first check valve disposed within the fluid passageway and biased towards a closed position;

a second check valve disposed within the fluid passageway and biased towards a closed position;

a pump bulb in fluid communication with the fluid passageway between the first and second check valves, wherein a negative pressure generated by an expansion of the pump bulb is sufficient to open the first check valve; and a reservoir chamber coupling the inlet to the fluid passageway, wherein a portion of the first check valve extends into the reservoir chamber and is coupled to an outer wall of the reservoir chamber so that as fluid pressure within the reservoir chamber increases, an expansion of the reservoir chamber occurs which urges the first check valve towards a closed position.

12. The prosthesis of claim 11 further including: a bar positioned within the housing and moveable between a first and a second position so that when the bar is moved from the first position to the second position the bar causes the first check valve to move from a closed position to an open position to deflate the implantable prosthesis, wherein the bar comprises a spring; a support member coupled to the housing and mechanically linked to the first check valve to prevent transverse movement of first check valve relative to the major axis of the fluid passageway when the first check valve is moving from an open to a closed position; and the first check valve is made of a metallic material with a plastic member disposed over a portion of the first check valve.

13. The prosthesis of claim 11 further including:

a spring coupling the first check valve to the outer wall;

the bar further comprising at least one rib extending across a bend such that a spring is created to afford the movement of the first check valve from a closed to an open position for deflation of the prosthesis.

14. The prosthesis of claim 11 wherein the spring is biased to maintain the first check valve in close proximity to the outer wall, and the biasing of the spring affording the intentional unseating of the first check valve after a pump bulb compression.

15. A penile prosthesis comprising:

a housing;

a fluid inlet to the housing, the fluid inlet being adapted to couple to a reservoir;

a fluid outlet from the housing, the fluid outlet being adapted to couple to an inflatable cylinder;

a reservoir chamber disposed within the housing and fluidly coupled to the inlet;

a fluid passageway with a major axis, the fluid passageway being fluidly coupled to the reservoir chamber;

a first check valve disposed within the fluid passageway and biased towards a closed position, the first check valve made of a metallic material with a plastic member disposed over a portion of the first check valve;

a second check valve disposed within the fluid passageway and biased towards a closed position;

a pump bulb in fluid communication with the fluid passageway between the first and second check valves;

a bar positioned within the housing and moveable between a first and a second position so that when the bar is moved from the first position to the second position the bar causes the first check valve to move from a closed position to an open position to deflate the implantable prosthesis, wherein the bar comprises a spring;

a support member coupled to the housing and mechanically linked to the first check valve to prevent transverse movement of first check valve relative to the major axis of the fluid passageway when the first check valve is moving from an open to a closed position, a spring biasing the first check valve into a sealed position, wherein the biasing force of the spring is selected to be strong enough to oppose pressures generated in an overpressurization situation and keep the first check valve in the sealed position; and a face coupled to the first check valve wherein the face has a large diameter compared to a diameter of the remainder of the first check valve so that suction forces generated after a compression of a pump bulb act on a sufficient surface area of the face to overcome the biasing force of the spring.

16. The prosthesis of claim 15 further including: a first lip seal located within the housing for selectively engaging an inner diameter portion of the face in a substantially fluid tight manner; and a second lip seal located within the housing for selectively engaging an outer diameter portion of the face in a substantially fluid tight manner.

* * * * *